(12) United States Patent  
Sarma et al.

(10) Patent No.: US 9,277,873 B2  
(45) Date of Patent: Mar. 8, 2016

(54) COMPUTATONAL TOOL FOR PRE-SURGICAL EVALUATION OF PATIENTS WITH MEDICALLY REFRACTORY EPILEPSY

(71) Applicant: The Johns Hopkins University, Baltimore, MD (US)

(72) Inventors: Sridevi V. Sarma, McLean, VA (US); Sandya Subramanian, Grand Rapids, MI (US); Stephanie Hao, Brier, WA (US)

(73) Assignee: The Johns Hopkins University, Baltimore, MD (US)

( * ) Notice: Subject to any disclaimer, the term of this patent is extended or adjusted under 35 U.S.C. 154(b) by 579 days.

(21) Appl. No.: 13/686,599

(22) Filed: Nov. 27, 2012

(65) Prior Publication Data

US 2014/0094710 A1    Apr. 3, 2014

Related U.S. Application Data

(60) Provisional application No. 61/744,739, filed on Oct. 3, 2012.

(51) Int. Cl.
| | |
|---|---|
| *A61B 5/04* | (2006.01) |
| *A61B 5/0476* | (2006.01) |
| *A61B 5/00* | (2006.01) |
| *A61B 5/0478* | (2006.01) |

(52) U.S. Cl.
CPC ............. *A61B 5/0476* (2013.01); *A61B 5/4064* (2013.01); *A61B 5/4094* (2013.01); *A61B 5/6868* (2013.01); *A61B 5/0478* (2013.01)

(58) Field of Classification Search
None
See application file for complete search history.

(56) References Cited

U.S. PATENT DOCUMENTS

2011/0130797 A1*  6/2011  Talathi et al. .................. 607/3
2012/0265262 A1* 10/2012  Osorio ............................ 607/3

OTHER PUBLICATIONS

Andrzejak R G, Chicharro D, Lehnertz K, Mormann F (2011) Using bivariate signal analysis to characterize the epileptic focus: The benefit of surrogates. Phys. Rev. E, 83:046203.

(Continued)

*Primary Examiner* — Etsub Berhanu
(74) *Attorney, Agent, or Firm* — Venable LLP; Henry J. Daley; Laura G. Remus

(57) ABSTRACT

A method of identifying an epileptogenic zone of a subject's brain includes receiving a plurality of electrical signals from a corresponding plurality of surgically implanted electrodes, calculating a first plurality of connectivities between each pair of electrodes based on a portion of each of the plurality of electrical signals corresponding to a first time period, assigning a rank corresponding to each electrode for the first period of time based on the first plurality of connectivities to provide a first plurality of ranks, calculating a second plurality of connectivities between each pair of electrodes based on a portion of each of the plurality of electrical signals corresponding to a second time period, assigning a rank corresponding to each electrode for the second period of time based on the second plurality of connectivities to provide a second plurality of ranks, identifying a cluster of electrodes among the plurality of electrodes based on relative changes between the first plurality of ranks from the first time period and the second plurality of ranks at the second time period, and identifying the epileptogenic zone based on the cluster of electrodes.

27 Claims, 12 Drawing Sheets

(56) References Cited

OTHER PUBLICATIONS

Arthuis M, Valtion L, Regis J, Chauvel P, Wendling F, Naccache L, Bernard C, Bartolomei F (2009) Impaired consciousness during temporal lobe seizures is related to increased long-distance cortical-subcortical synchronization. Brain, 132:2091:2101.

Baier G, Muller M, Stephani U, Muhle H (2007) Characterizing correlation changes of complex pattern transitions: The case of epileptic activity. Phys. Let. A, 363:290-296.

Bancaud J, Angelergues R, Bernouilli C, Bonis A, Bordas-Ferrer M, Bres-son M, Buser P, Covello L, Morel P, Szikla G, Takeda A, Talairach J. (1970) Functional stereotaxic exploration (SEEG) of epilepsy. Electro-encephalogr Clin Neurophysiol 28:85-86.

Begley CE, Famulari M, Annegers JF, Lairson DR, Reynolds TF, Goan S, Dubinsky S, Newmark ME, Leibson C, So EL, Rocca WA.. The cost of epilepsy in the United States: an estimate from population-based clinical and survey data. Epilepsia 2000;41: 342-351.

Bendat J S, Piersol A G (1986) Random Data: Analysis and Measurement Procedures, 2nd edition, John Wiley & Sons: New York, NY.

Berg AT, Kelly MM. Defining intractability: comparisons among published definitions. Epilepsia. Feb. 2006;47(2):431-6.

Berg, AT. Identification of Pharmacoresistant Epilepsy. Neurol Clin 27 (2009) 1003-1013.

Boonyapisit K, Najm I, Klem G, Ying Z, Burner C, LaPresto E, Nair D, Bingaman W, Prayson R, Luders H. (2003) Epileptogenicity of focal malformations due to abnormal cortical development: direct electrocorticographic-histopathologic correlations. Epilepsia. 44(1):69-76.

Brodie, M.J., Shorvon, S.D., Ganger, R. et al. Commission on European Affairs: appropriate standards of epilepsy care across Europe. Epilepsia 1997;28:1245-1250.

Bulacio J, Jehi L, Wong C, Gonzalez-Martinez J, Kotagal P, Nair D, Najm I, Bingaman W. Long-term seizure outcome after resective surgery in patients evaluated with intracranial electrodes. Epilepsia. 2012.

Cohen, J., Cohen P., West, S.G., & Aiken, L.S. (2003). Applied multiple regression/correlation analysis for the behavioral sciences. (2nd ed.) Hillsdale, NJ: Lawrence Erlbaum Associates.

Engel, J. et al., 1990. Presurgical evaluation for partial epilepsy: relative contributions of chronic depth-electrode recordings versus FDG-PET and scalp-sphenoidal ictal EEG. Neurology, 40(11), pp. 1670-1677.

Gilliam FG, Kuzniecky R, Meador K. Patient-oriented outcome assessment after temporal lobectomy for refractory epilepsy. Neurology 1999;53:687-94.

Gilliam FG. Diagnosis and treatment of mood disorders in persons with epilepsy. Curr Opin Neurol. Apr. 2005;18(2):129-33.

Gonzalez-Martinez J, Bingaman W, Steven T, Najm I. Neurogenesis in the postnatal human epileptic brain. J Neurosurg. Sep. 2007;107(3):628-35.

Gonzalez-Martinez JA, Hugher G, Chen T, Bulacio J, So N, Bingaman W, Jehi, L, Hantus S, Najm I. Invasive monitoring using depth electrodes at a Noth American Center: A prospective study analyzing the feasibility and safety of stereo-electroencephalography (SEEG) in the diagnosis and treatment of intractable epilepsy. Epilepsia 2010 AES abstracts.

González-Martínez JA, Möddel G, Ying Z, Prayson RA, Bingaman WE, Najm IM. Neuronal nitric oxide synthase expression in resected epileptic dysplastic neocortex. J Neurosurg. Feb. 2009;110(2):343-9.

González-Martínez JA, Srikijvilaikul T, Nair D, Bingaman W. Long-term seizure outcome in reoperation after failure of epilepsy surgery. Neurosurgery. May 2007; 60(5):873-80; discussion 873-80.

González-Martínez JA, Ying Z, Prayson R, Bingaman W, Najm I. Glutamate Clearence mechanisms in resected cortical dysplasia. J Neurosurg. Nov. 12, 2011.

Hermann BP, Seidenberg M, Dow C, Jones J, Rutecki P, Bhattacharya A, Bell B. Cognitive prognosis in chronic temporal lobe epilepsy. Ann Neurol. Jul. 2006;60(1):80-7.

Jeha LE, Najm I, Bingaman W, Dinner D, Widdess-Walsh P. Surgical outcome and prognostic factors of frontal lobe epilepsy surgery. Brain (2007);130:574-584.

Jeha, L E et al., 2006. Predictors of outcome after temporal lobectomy for the treatment of intractable epilepsy. Neurology, 66(12), pp. 1938-1940.

Jung, Won Young; Pacia, Steven V.*; Devinsky, Orrin* (1999) Neocortical Temporal Lobe Epilepsy: Intracranial EEG Features and Surgical Outcome. Journal of Clinical Neurophysiology: Sep. 1999—vol. 16—Issue 5—p. 419.

Kahane P, Minotti L, Hoffmann D, Lachaux JP, Ryvlin P. (2004) Invasive EEG in the definition of the seizure onset zone: depth electrodes. In: Rosenow F, Lüders H (Eds) Presurgical assessment of the epilepsies with clinical neurophysiology and functional imaging. Elsevier, Amsterdam, The Netherlands, pp. 109-133.

Kellinghaus C, Moddel G, Shigeto H, Ying Z, Jacobsson B, Gonzalez-Martinez J, Burrie C, Janigro D, Najm I. Dissociation between in vitro and in vivo epileptogenicity in a rat model of cortical dysplasia. Epileptic Disord. Mar. 2007; 9(1):11-9. Epub Feb. 15, 2007.

Kerfoot C, Vinters H, Mathern G (1999) Cerebral cortical dysplasia: giant neurons show potential for increased excitation and axonal plasticity. Dev. Neurosci 21: 260-270.

Kerr M, Burns S, Gale J, Sarma SV (2011) Multivariate Analysis of SEEG Signals During Seizure. Proceedings of the 33rd IEEE EMBS Conference.

Kramer M A, Eden U T, Kolaczyk E D, Zepeda R, Eskandar E N, Cash S S (2010) Coalescence and fragmentation of cortical networks during focal seizures. J. Neurosci., 30(30):10076-10085.

Kramer M A, Kolaczyk E D, Kirsch H E (2008) Emergent network topology at seizure onset in humans. Epilepsy Res., 79:173-186.

Kwan P, Brodie MJ. Early identification of refractory epilepsy. N Engl J Med. Feb. 3, 2000;342(5):314-9.

Lüders HO, Najm I, Nair D, Widdess-Walsh P, Bingman W. The epileptogenic zone: general principles. Epileptic Disord. Aug. 2006;8 Suppl 2:S1-9. Erratum in: Epileptic Disord. Jun. 2008;10(2):191.

MacQueen, J. B. (1967). Some Methods for classification and Analysis of Multivariate Observations. Proceedings of 5th Berkeley Symposium on Mathematical Statistics and Probability. University of California Press. pp. 281-297.

Mathern GW, Babb TL, Pretorius JK (1995) Reactive synaptogenesis and neuron densities for neuropeptide Y, somatostatin, and glutamate decarboxylase immunoreactivity in the epileptogenic human fasciadentata. J Neurosci 15:3990-4004.

McIntosh AM, Kalnins RM, Mitchell LA, Fabinyi GC, Briellmann RS, Berkovic SF. Temporal lobectomy: long-term seizure outcome, late recurrence and risks for seizure recurrence. Brain. Sep. 2004;127(Pt 9):2018-30. Epub Jun. 23, 2004.

Mikuni N, Babb TL, Ying Z, Najm I, Nishiyama K, Wylie C, Yacubova K, Okamoto T, Bingaman W (1999) NMDA-receptor 1 and 2A/B coassembly increased in human epileptic focal cortical dysplasia. Epilepsia 40: 1683-1687.

Moddel G, Jacobson B, Ying Z, Janigro D, Bingaman W, Gonzalez-Martinez J, Kellinghaus C, Prayson R, Najm I. The NMDA Recepter NR2B Subunit Contributes to Epileptogenesis in Human Cortical Dysplasia. Brain Res. Jun. 7, 2005;1046(1-2):10-23.

Murray MI, Halpern MT, Leppik IE. Cost of refractory epilepsy in adults in the USA. Epilepsy Research. 1996; 23:139-148.

Nair DR, Burgess R, McIntyre CC, Lüders H. (2008) Chronic subdural electrodes in the management of epilepsy. Clin Neurophysiol 119: 11-28.

Najm I, Bingaman W, Lüders H. (2002) the use of subdural grids in the management of focal malformations due to abnormal cortical develop-ment. Neurosurg Clin N Am 13:87-92.

Najm I, Ying Z, Babb T, Mohamed A, LaPresto E, Wyllie E, Kotagal P, Bingaman W, Foldvary N, Morris H, Lüders H. NMDA receptor 2A/B subtype differential expression in human cortical dysplasia: Correlation with in situ epileptogenicity. Epilepsia 2000;41:971-976.

Najm I, Ying Z, Boonyapisit K, Bingaman W, Prayson R, Lüders H. Malformations due to abnormal cortical development: Expression and mechanisms of epileptogenicity. Advances in Clinical Neurophysiology, 2002, 54:462-469.

(56) References Cited

OTHER PUBLICATIONS

Netoff T I, Schiff S J (2002) Decreased Neuronal Synchronization during Experimental Seizures. J Neurosci., 22(16):7297-7307.
Onal C, Otsubo H, Araki T, Chitoku S, Ochi A, Weiss S, Elliott I, Snead OC, Rutka JT, Logan W. (2003) Complications of invasive subdural grid monitoring in children with epilepsy. J Neurosurg 98:1017-1026.
Palmini A, Gambardella A, Andermann F, Dubeau F,da Costa JC, Olivier A, Tampieri D, Gloor P, Quesney F, Andermann E. (1995) Intrinsic epileptogenicity of human dysplastic cortex as suggested by corticography and surgical results. Ann Neurol 37: 476-487.
Penfield W, Jasper H H (1954) Epilepsy and the functional anatomy of the human brain. Boston: Little Brown.
Ponten S C, Bartolomei F, Stam C J (2007) Small-world networks and epilepsy: Graph theoretical analysis of intracerebrally recorded mesial temporal lobe seizures. Clin. Neurophys., 118:918-927.
Prayson RA, Estes ML (1995) Cortical dysplasia: a histopathologic study of 52 cases of partial lobectomy in patients with epilepsy. Hum Pathol. 26(5):493-500.
Risinger M, Gumnit R. (1995) Intracranial electrophysiologic studies. Neu-roimaging Clin N Am 5:559-573.
Rosenow F, Luders H. Pre-surgical evaluation of epilepsy. Brain 2001; 124 (Pt 9):1683-700.
Santaniello S, Burns SP, Golby J, Singer J, Anderson WS, Sarma SV. (2011) Quickest Detection of Seizure Onsets in Drug-Resistant Patients: An Optimal Control Approach. Epilepsy & Behavior, 22, pp. 49-60.
Schevon C A, Cappell J, Emerson R, Isler J, Grieve P, Goodman R, Mckhann G, Weiner H, Doyle W, Kuzniecky R, Devinsky O, Gilliam F (2007) Cortical abnormalities in epilepsy revealed by local EEG synchrony. NeuroImage, 35:140:148.
Schiff S J, Sauer T, Kumar R, Weinstein S L (2005) Neuronal spatiotemporal pattern discrimination: The dynamical evolution of seizures. NeuroImage, 28:1043-1055.
Schindler K A, Bialonski S, Horstmann M T, Elger C E, Lehnertz K (2008) Evolving functional network properties and synchronizability during human epileptic seizures. Chaos, 18:033119.
Schuele SU, Lüders HO. Intractable epilepsy: management and therapeutic alternatives. Lancet Neurol. Jun. 2008;7(6):514-24.
Taylor, DC, Falconer, MA, Bruton, CJ, Corsellis JA (1997) Focal dysplasia of the cerebral cortex in epilepsy. J. Neurol Neurosurg Psychiatry. 34: 369-387.
Urbacj H, Hattinggen J, von Oertzen, et al, MR imaging in the presurgical workup of patients with drug-resistant epilepsy, AJNR 25:919-926 Jun./Jul. 2004.
Warren C P, Hu S, Stead M, Brinkmann B H, Bower M R, Worrell G A (2010) Synchrony in normal and focal epileptic brain: the seizure onset zone is functionally disconnected. J. Neurophysiol., 104:3530-3539.
Wendling F, Bellanger J J, Badier J M, Coatrieux J L (1996) Extraction of spatio-temporal signatures from depth EEG seizure signals based on objective matching in warped vectorial observations. IEEE Trans. Biomed. Eng., 43(10):990-1000.
Widdess-Walsh P, Jeha L, Nair D, Kotagal P, Bingaman W, Najm I. Subdural electrode analysis in focal cortical dysplasia: predictors of surgical outcome. Neurology. Aug. 14, 2007;69(7):660-7.
Wieser. Epilepsy surgery: past, present and future. Seizure: European Journal of Epilepsy. vol. 7, Issue 3 , pp. 173-184, Jun. 1998.
Wu L, Gotman J (1998) Segmentation and classification of EEG during epileptic seizures. Electroenceph. Clin. Neurophys., 106:344-356.
Ying Z, Babb TL, Comair YG, Bingaman W, Bushey M, Touhalisky K (1998) Induced expression of NMDAR2 proteins and differential expression of NMDAR1 splice variants in dysplastic neurons of human epileptic neocortex. J Neuropath Exp Neurol 57:47-62.
Ying Z, Babb TL, Mikuni N, Najm I, Drazba J, Bingaman W. Selective co-expressions of NMDAR2A/B and NMDAR1 subunit proteins in dysplastic neurons of human epileptic cortex. Experimental Neurology, 159: 409-418, 1999.
Ying Z, Gonzalez-Martinez J, Bingaman W, Najm I. Expression of Neuronal Stem Cell Surface Marker CD133 in balloon cells of human focal cortical dysplasia. Epilepsia. Nov. 2005;46(11):1716-23.
Zaveri H P, Pincus S M, Goncharva I I, Duckrow R B, Spencer D D, Spencer S S (2009) Localization-related epilepsy exhibits significant connectivity away from the seizure-onset area. NeuroReport, 20:891-895.
Ferro et al., "Depressive symptoms among mothers of children with epilepsy: A review of prevalence, associated factors, and impact on children," Epilepsia, 50 (11): 2344-2354, 2009.
Yaffe et al., "Brain State Evolution During Seizure and under Anesthesia: A Network-Based Analysis of Stereotaxic EEG Activity in Drug-Resistant Epilepsy Patients," Proceedings of the 34th IEEE EMBS Conference, Aug. 28-Sep. 1, 2012, pp. 5158-5161.

\* cited by examiner

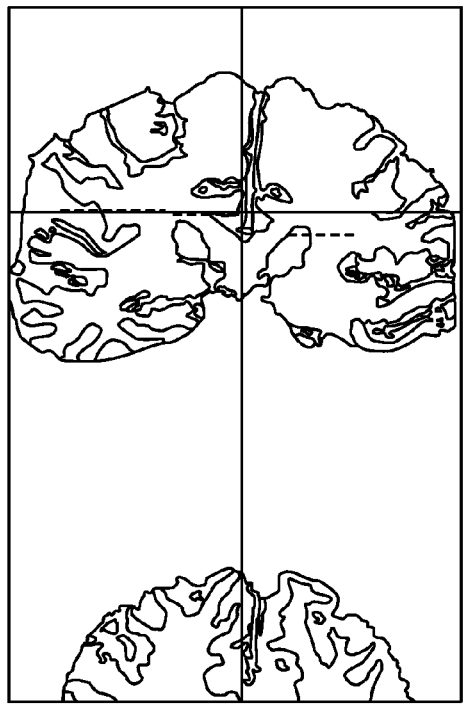 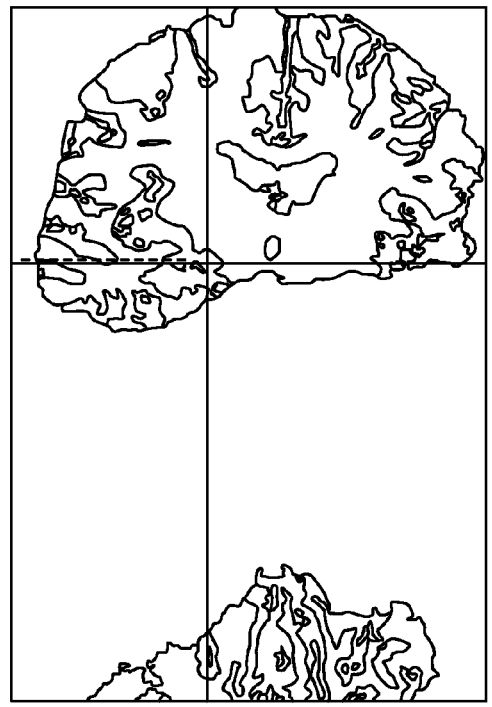
FIG. 1A  FIG. 1B
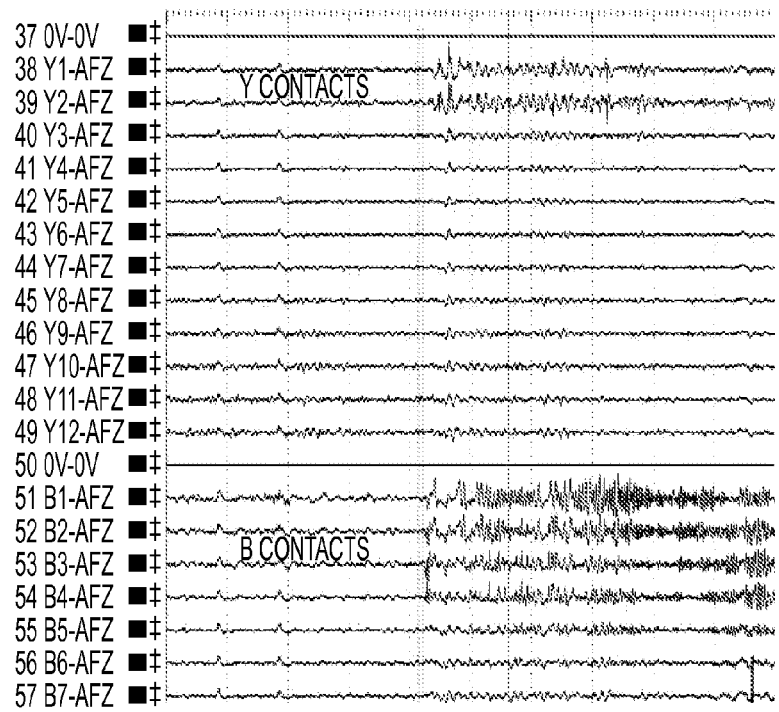
FIG. 1C

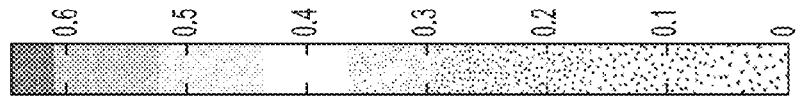
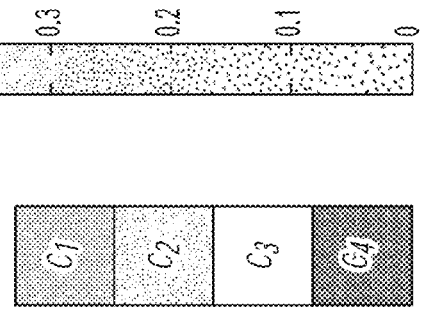
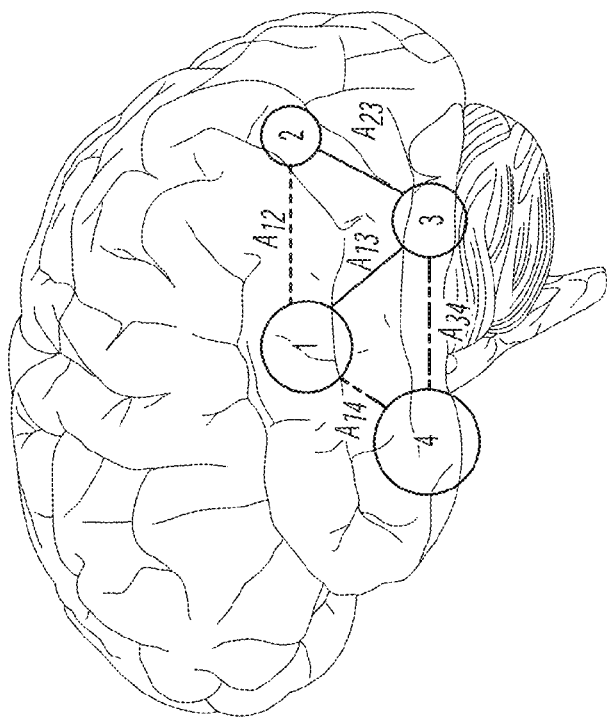
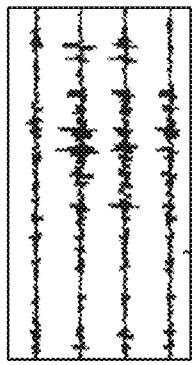
FIG. 4D
FIG. 4B
FIG. 4A
FIG. 4C

| TABLE – EZTrack EXEMPLAR RESULTS | | | | | | | | |
|---|---|---|---|---|---|---|---|---|
| IMPLANTATION METHODOLOGY | SEIZURE TYPE | AGE, SEX | # SEIZURES ANALYZED | # ELECTRODES | DURATION OF EEG RECORDINGS | EZ CLUSTER SIGNATURE | EZTrack's OUTCOME PREDICTION, ACTUAL OUTCOME - AIM 1 | EZTrack's LOCALIZATION PERFORMANCE (SENS, SPEC) - AIM 2 |
| SEEG | CPS | 38M | 5 | 93 | 2.8 HRS | ~ | SUCCESS, SUCCESS | (0.9, 1) |
| SEEG | CPS | 32F | 4 | 57 | 1.9 HRS | ~ | FAILURE, SUCCESS | (1, 1) |
| SEEG | CPS-SG | 49F | 6 | 82 | 4.7 HRS | ~ | SUCCESS, SUCCESS | (1, 1) |
| SEEG | CPS | 23M | 3 | 71 | 1.4 HRS | ~ | FAILURE, FAILURE | (0.4, 1) |
| SEEG | CPS | 57M | 7 | 61 | 2.7 HRS | ~ | SUCCESS, SUCCESS | (0.81, 1) |
| SEEG TOTAL | | | 25 | 354 | 13.5 HRS | | | (0.83, 1) |
| SDE | UNKNOWN | 18M | 3 | 86 | 2.1 HRS | ~ | FAILURE, FAILURE | (0.83, 0.84) |
| SDE | CPS | 17F | 2 | 40 | 1.4 HRS | ~ | SUCCESS, SUCCESS | (1, 0.83) |
| SDE | CPS-SG | 49F | 4 | 82 | 0.8 HRS | ~ | FAILURE, FAILURE | (1, 0.713) |
| SDE | CPS-SG | 14M | 7 | 99 | 0.85 HRS | ~ | SUCCESS, SUCCESS | (0.83, 0.83) |
| SDE | CPS | 22M | 3 | 24 | 1.5 HRS | ~ | SUCCESS, SUCCESS | (1, 0.7) |
| SDE TOTAL | | | 19 | 331 | 6.65 | | | (0.9, 0.82) |
| TOTAL | | | 44 | 685 | 20.15 | | | (0.9, 0.82) |

FIG. 9

COMPUTATONAL TOOL FOR PRE-SURGICAL EVALUATION OF PATIENTS WITH MEDICALLY REFRACTORY EPILEPSY

CROSS-REFERENCE OF RELATED APPLICATION

This application claims priority to U.S. Provisional Application No. 61/744,739 filed Oct. 3, 2012, the entire content of which is hereby incorporated by reference.

BACKGROUND

1. Field of Invention

The field of the currently claimed embodiments of this invention relates to methods and systems for evaluating epileptic zones of a subject's brain.

2. Discussion of Related Art

Epilepsy is one of the most common brain disorders, characterized by chronically recurrent seizures resulting from excessive electrical discharges from groups of neurons [1]. Epilepsy affects about 50 million people worldwide and approximately 40% of all individuals with epilepsy have intractable seizures, which cannot completely be controlled by medical therapy [2-4]. That is, seizures continue to occur despite treatment with a maximally tolerated dose of at least two anti-epilepsy drugs (AEDs). The direct cost of assessing and treating patients with medically refractory epilepsy (MRE) ranges from $3-4 billion annually ($16 billion in direct and indirect costs) in the US (based on a 1996 publication) [5]. 80% of these costs are accounted by patients whose seizures are not adequately controlled by AEDs [6]. The burden of MRE, however, is much greater than heavy financial costs. MRE is a debilitating illness where individuals lose their independence, causing profound behavioral, psychological, social, financial and legal issues [7-11]. Recurrent seizures impair socialization and psychological development during formative years and may lead to an inability to obtain an education, gainful employment, or driving privileges. The development of a learned helplessness and low self-esteem can worsen as long as epilepsy is intractable. Cognitive performance may be impaired by MRE as well as by side effects of AED therapy [7-11].

Surgical Treatment of MRE

Despite the heavy sequelae from MRE, there is a potentially curative procedure—surgical resection of the epileptogenic zone (EZ), which is the minimal area of brain tissue responsible for generating the recurrent seizure activity [12]. However, to be effective, this procedure depends on correct identification of the EZ, which is often unclear. A comprehensive pre-surgical evaluation is necessary to pinpoint the EZ as well as to identify the risk of neurologic morbidity such as visual impairment. Various non-invasive and invasive methods are used. Non-invasive techniques include scalp EEG, video-EEG, neuropsychological tests, speech-language studies, and brain imaging (MRI, PET, Ictal SPECT). Of these methods, the highest predictor of surgical success is identification of a single visible MRI lesion [13], yet despite the advances in imaging technologies, a significant number of surgical patients with focal epilepsy (~25%) continue to have normal MRIs [14-17].

When the less invasive methods fail to identify the EZ, the method of last resort is an invasive evaluation, comprising placement of subdural grid electrodes (SDE) or stereotactically placed depth electrodes (stereoelectroencephalography, a.k.a. SEEG) and subsequent prolonged extra-operative monitoring in a dedicated Epilepsy Monitoring Unit (EMU) [41]. Subdural grids and strips are the most common invasive method used in the United States [18, 41-43, 46]. Despite the high spatial resolution provided by the subdural methodology, which allows for accurate mapping of superficial cortical areas, relatively deep epileptic foci cannot be sampled with adequate spatial and temporal resolution. In addition, subdural grids require relative large craniotomies and are, in general, limited to exploration of one hemisphere. There thus remains a need for improved systems and methods for evaluating epileptic zones of a subject's brain.

SUMMARY

A method of identifying an epileptogenic zone of a subject's brain according to an embodiment of the current invention includes receiving a plurality of electrical signals from a corresponding plurality of surgically implanted electrodes, calculating a first plurality of connectivities between each pair of electrodes based on a portion of each of the plurality of electrical signals corresponding to a first time period, assigning a rank corresponding to each electrode for the first period of time based on the first plurality of connectivities to provide a first plurality of ranks, calculating a second plurality of connectivities between each pair of electrodes based on a portion of each of the plurality of electrical signals corresponding to a second time period, assigning a rank corresponding to each electrode for the second period of time based on the second plurality of connectivities to provide a second plurality of ranks, identifying a cluster of electrodes among the plurality of electrodes based on relative changes between the first plurality of ranks from the first time period and the second plurality of ranks at the second time period, and identifying the epileptogenic zone based on the cluster of electrodes.

A computer-readable medium for identifying an epileptogenic zone of a subject's brain according to an embodiment of the current invention includes non-transitory computer-executable code. The code, when executed by a computer, causes the computer to receive a plurality of electrical signals from a corresponding plurality of surgically implanted electrodes, calculate a first plurality of connectivities between each pair of electrodes based on a portion of each of the plurality of electrical signals corresponding to a first time period, assign a rank corresponding to each electrode for the first period of time based on the first plurality of connectivities to provide a first plurality of ranks, calculate a second plurality of connectivities between each pair of electrodes based on a portion of each of the plurality of electrical signals corresponding to a second time period, assign a rank corresponding to each electrode for the second period of time based on the second plurality of connectivities to provide a second plurality of ranks, identify a cluster of electrodes among the plurality of electrodes based on relative changes between the first plurality of ranks from the first time period and the second plurality of ranks at the second time period, and identify the epileptogenic zone based on the cluster of electrodes.

A system for identifying an epileptogenic zone of a subject's brain according to an embodiment of the current invention includes a computer configured to receive a plurality of electrical signals from a corresponding plurality of surgically implanted electrodes, calculate a first plurality of connectivities between each pair of electrodes based on a portion of each of the plurality of electrical signals corresponding to a first time period, assign a rank corresponding to each electrode for the first period of time based on the first plurality of connectivities to provide a first plurality of ranks, calculate a second plurality of connectivities between each pair of electrodes based on a portion of each of the plurality of electrical signals corresponding to a second time period, assign a rank corresponding to each electrode for the second period of time based on the second plurality of connectivities to provide a second plurality of ranks, identify a cluster of electrodes among the plurality of electrodes based on relative changes between the first plurality of ranks from the first time period and the second plurality of ranks at the second time period, and identify the epileptogenic zone based on the cluster of electrodes.

BRIEF DESCRIPTION OF THE DRAWINGS

Further objectives and advantages will become apparent from a consideration of the description, drawings, and examples.

FIGS. 1A-1C show SEEG electrode placement (A and B) and their respective recordings during an seizure (C). Electrodes were anatomically placed in the posterior cingulated gyms (A) and Hippocampus (B). Note the simultaneous ictal onset in both regions (C).

FIGS. 3A and 3B show pre-op imaging with MRA and angiography, respectively. Together, electrode trajectories are safely planned, avoiding vascular structures, and limiting the risk of bleeding and electrode misplacement. FIG. 3C is a photograph showing 14 electrodes at the skin surface. FIG. 3D is an intraoperative image showing a superposition of bilateral SEEG electrodes on a coronal MRI T1W image. Note the precise parallel placement, with tips terminating at the midline or dural surface.

FIGS. 4A-4D provide a schematic illustration of Network Analysis according to an embodiment of the current invention. 4A) EEG traces from 4 electrodes during 5 second window. 4B) Corresponding graph with edge weights computed from EEG. 4C) Matrix representation of graph, where $A_{ij}$ quantifies dependence between EEG signals in electrodes i and j. 4D) Corresponding centrality $C_i$ of each node i in graph. Note that electrodes 1 and 4 have largest centrality as seen by their superior connectedness in graph either by number of edges (node 1) or edge weights (node 4).

FIG. 9 is a table of results according to an embodiment of the current invention.

DETAILED DESCRIPTION

Figure 2:
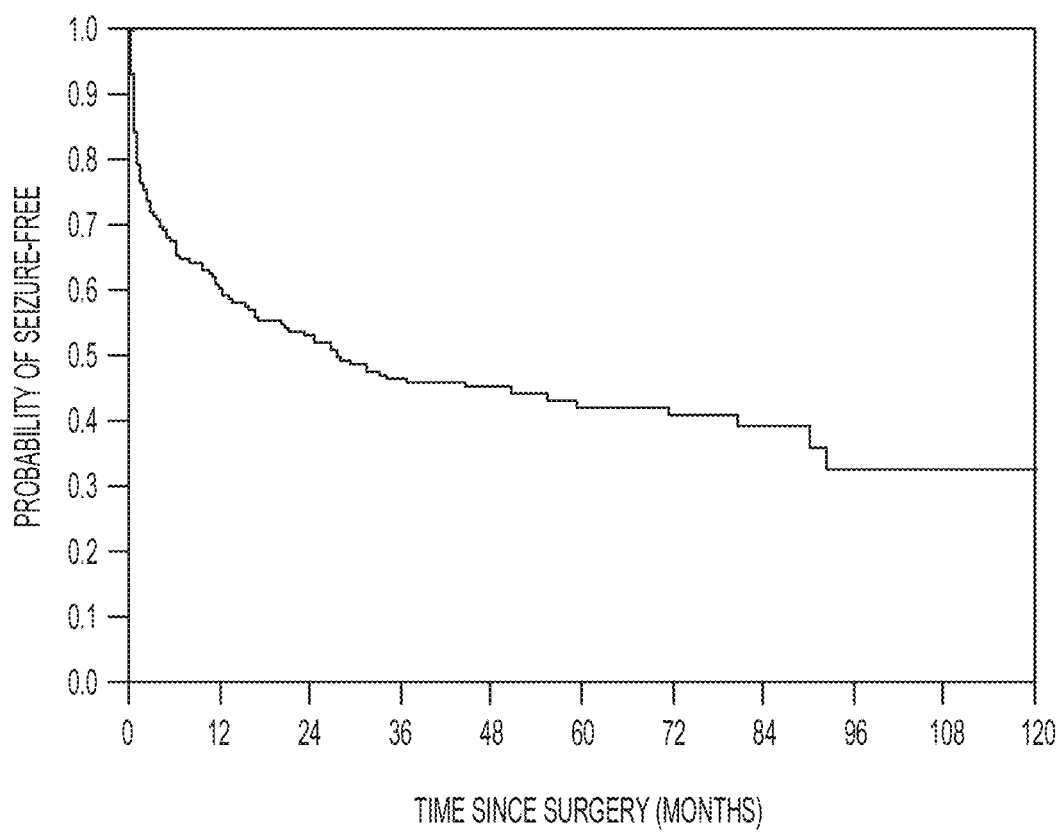
FIG. 2 provides a Kaplan-Meier plot illustrating chances of postoperative seizure freedom following resective surgery in all patients evaluated with intracranial electrodes following invasive evaluation [41].

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

We explored alternative/complementary methods for invasive monitoring, according to some embodiments of the current invention, revisiting the concepts and the techniques of the SEEG methodology used more extensively in Europe [44, 45]. We describe the SEEG methodology in more detail below. However, some embodiments can provide a tool that can be applied to any invasive EEG signals.

Invasive evaluations are very expensive, and are associated with multiple complications including bleedings, infections, and neurological deficits [46, 47]. Although the placement of, and recordings from, intracranial electrodes should significantly improve our ability to localize and delineate the extent of the EZ, a failure to accomplish this goal is not uncommon and is due to (i) limited spatial sampling resulting from the relatively small number of electrodes that can be safely inserted and/or a wrong pre-implantation electro-clinical hypothesis, and (ii) incorrect identification of EZ signatures from intracranial EEG recordings.

According to some embodiments of the current invention, we address reason (ii) for failures and focus on patients at the Cleveland Clinic in the following examples that are selected for SDE or SEEG implantation with a strong pre-implantation hypothesis of the location of the EZ, minimizing the spatial sampling limitation. Therefore, in these patients, there is adequate coverage of the brain and surgical outcome hinges on the ability to identify EZ signatures from the invasive EEG recordings.

The conventional process of identifying the EZ involves visually inspecting tens to hundreds of EEG signals without the assistance of computational tools (FIG. 1). Epileptologists study the onset of seizure events that occur over several days. Seizure events are typically marked by the early presence of beta-band activity ('beta buzz') or bursts of high frequency oscillations (100-300 Hz) [20]. Assuming the EZ generates epileptiform activity, which then entrains other regions into a clinical seizure [19, 20], channels where these onset features first appear are commonly identified as the EZ. Electrodecremental responses (loss of rhythmic activity) are also often observed. In general, epileptologists look at a variety of signatures to make their decision [20].

Despite all of these possible EEG signatures, localizing the EZ may remain unclear. For example, FIG. 1 shows an example of unclear localization of the EZ in a patient with MRE. Both Y contacts, located in the cingulate gyrus (FIGS. 1A) and B contacts, located in the mesial temporal lobe (FIG. 1B) demonstrated simultaneous paroximal fast activity during a seizure (ictal) event, resulting in imprecise seizure localization. In this patient, no surgical resection was proposed due to the unclear anatomical EZ localization.

The Cleveland Clinic is a busy epilepsy center that performs hundreds of surgical resections a year using both SDE and SEEG pre-surgical evaluation. FIG. 2 shows long-term postoperative seizure-freedom rates in 336 well-described intractable epilepsy patients treated at the Cleveland Clinic and followed up for 10 years [41]. A very rapid initial seizure recurrence rate, likely caused by non-identification and/or non-resection of the EZ, accounts for a significant portion of these surgical failures, and 40% of all recurrences occurred within 6 months of surgery. As such, any intervention aimed at improving the pre-operative localization of the EZ, and thus slowing down the initial steep recurrence phase observed after surgery, would greatly improve patient outcomes. Seizure recurrences that occur after 6 months may be attributed to neo-epileptogenesis, wherein secondary circuitry may take over forming a secondary EZ in a predisposed dormant brain tissue, which was left behind after the initial surgery. At this point, a patient may be considered for a second surgery.

An embodiment of the current invention provides a method of identifying an epileptogenic zone of a subject's brain. The method includes receiving a plurality of electrical signals from a corresponding plurality of surgically implanted electrodes, calculating a first plurality of connectivities between each pair of electrodes based on a portion of each of the plurality of electrical signals corresponding to a first time period, assigning a rank corresponding to each electrode for the first period of time based on the first plurality of connectivities to provide a first plurality of ranks, calculating a second plurality of connectivities between each pair of electrodes based on a portion of each of the plurality of electrical signals corresponding to a second time period, assigning a rank corresponding to each electrode for the second period of time based on the second plurality of connectivities to provide a second plurality of ranks, identifying a cluster of electrodes among the plurality of electrodes based on relative changes between the first plurality of ranks from the first time period and the second plurality of ranks at the second time period, and identifying the epileptogenic zone based on the cluster of electrodes.

The plurality of surgically implanted electrodes can be implanted by the SDE or SEEG methods, for example. Some examples will be described in more detail below.

In some embodiments, the calculating the first plurality of connectivities calculates a connectivity matrix by using the formula $$A_{ij} = \int_{50Hz}^{90Hz} P_i(f) P_j(f) df$$

where $P_i$, $P_j$ are magnitudes of Fourier transforms of said portion of said electrical signal corresponding to said first time period from electrodes i, and j respectively, of said plurality of electrodes. (To compute these pairwise connectivity weights, we can also use other measures such as cross-coherence in a frequency band, peak time correlation, mutual information etc. The general concepts are not limited only to cross power.) The calculating the second plurality of connectivities can be calculated in the same way using the same equation. This can be repeated for many time periods providing a time-dependent representation of $A_{ij}$. However, the general concepts of the current invention are not limited to connectivities calculated as in the equation above. Further, different integration limits can be selected in other embodiments of the current invention.

Some embodiments can further include calculating time-dependent eigenvectors corresponding to the time-dependent connectivity matrix. In some embodiments, the time-dependent eigenvectors can be converted into ranked time-dependent eigenvectors. Some embodiments can further include forming a correlation matrix based on the ranked time-dependent eigenvectors. Further embodiments can include identifying the cluster of electrodes based on the correlation matrix.

A computer-readable medium for identifying an epileptogenic zone of a subject's brain according to some embodiments of the current invention includes non-transitory computer-executable code that, when executed by a computer causes the computer to perform the above-noted methods. A system for identifying an epileptogenic zone of a subject's brain according to some embodiments of the current invention includes a computer configured to perform the above-noted methods.

Further additional concepts and embodiments of the current invention will be described by way of the following examples. However, the broad concepts of the current invention are not limited to these particular examples.

EXAMPLES

Intracranial EEG Dynamic Network Analysis Offers Assistance for EZ Localization

Recently, we showed that intracranial EEG is rich in information beyond the typical signatures clinicians use to identify the EZ [21-23]. In particular, by viewing the epileptic brain as a dynamic networked system where EEG signals are correlated both temporally and spatially, we have constructed a set of network-based statistics whose temporal evolution distinguishes the epileptic regions from the non-epileptic regions (see below for some more details). We used these tome series statistics to develop a binary classification tool, EZTrack, that has been tested on 5 patients implanted with SDE and 5 patients implanted with SEEG electrodes. For SEEG patients, EZtrack according to en embodiment of the current invention achieved an overall performance of 88% sensitivity and 100% specificity when its predicted EZ was compared to post-resection seizure outcome and histological reports of resected tissue. For the SDE patients EZTrack's predictions of the EZ were compared to resected regions (no histology reports available) and it achieved 90% sensitivity and 82% specificity. The latter test assumed that all resected regions have pathological structure, which may not be the case. For an SEEG patient, EZTrack predicted that part of the resected tissue (deemed pathological by clinicians) was normal, which was confirmed by histological analyses. Finally, a minimum of 2 seizures per patient were used to obtain these results, which translated to an average duration of processing 2.01 hours of EEG recordings. Therefore, EZTrack according to some embodiments of the current invention can not only reduce extra-operative monitoring time in the EMU, thereby cutting medical costs and decreasing complications associated with invasive monitoring, but can also decrease localization failures, allowing for more focal resections with less morbidity.

EZTrack, according to some embodiments of the current invention, can also have a global impact as epilepsy surgery is less likely to be considered in developing countries, whether because of a lack of resources or because many physicians do not recognize that a treatable syndrome exists [24]. There has been a recent expansion in epilepsy surgery in the so-called developed countries due to the availability of advanced non-invasive diagnostic tools to delineate epileptogenic lesions and epilepsy-related functional deficits, and to prove epileptogenicity [24]. EZTrack, according to some embodiments of the current invention, can provide portable software that can make available to all countries an advanced diagnostic tool to assist invasive monitoring.

In summary, some embodiments of the current invention can be highly significant because:

A significant number of epilepsy patients do not respond to drugs, leaving them severely impaired.

The only alternative for many of these patients is surgical resection of the EZ, which has significant short-term seizure recurrence, and whose pre-surgical evaluation is too invasive, causing increased morbidity, hospital resources, and patient costs.

Some embodiments of the current invention may increase success rates of surgery, and minimize pre-surgical evaluation invasiveness and time, resulting in significantly increased quality of life.

Some embodiments of the current invention may also change the standard practice of surgical resections in the developed countries, requiring less resources and specialized expertise from clinicians, and may eventually enable developing regions to better treat MRE.

The following examples summarize some embodiments of the current invention. First, we describe a novel and minimally invasive method of extra-operative intracranial EEG monitoring (SEEG) according to an embodiment of the current invention. Second, we describe a novel application of graph theory and network dynamics to develop our binary classification tool that identifies the EZ from invasive EEG recordings—EZTrack according to an embodiment of the current invention. Then, we discuss how, in validating EZTrack, we can examine pathological markers in resected tissue that delineate resected brain regions identified as "Epileptic" or "Non-Epileptic," an investigation that, to our knowledge, has not been done before.

The Stereotactic Placement of Depth Electrodes.

The Cleveland Clinic is a world-renowned center for the evaluation and treatment of epilepsy, assessing around 9,500 patients every year from all 50 states and more than 10 countries. More than 400 associated epilepsy surgeries are performed every year, including a growing number of stereotactically placed EEG (SEEG) electrodes [44, 45], a technique that was developed in France, and brought to the United States by Dr. Jorge Gonzalez-Martinez. No other institutions within North America use this method.

Figure 3B:
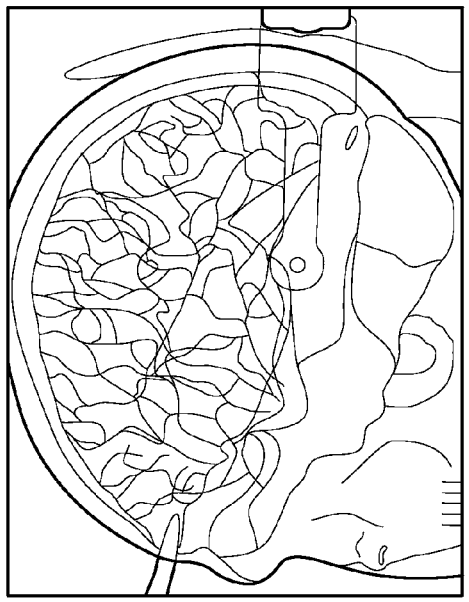
FIGS. 3A-3D show imaging fusion and placement of multiple electrodes using the SEEG method.
Figure 3D:
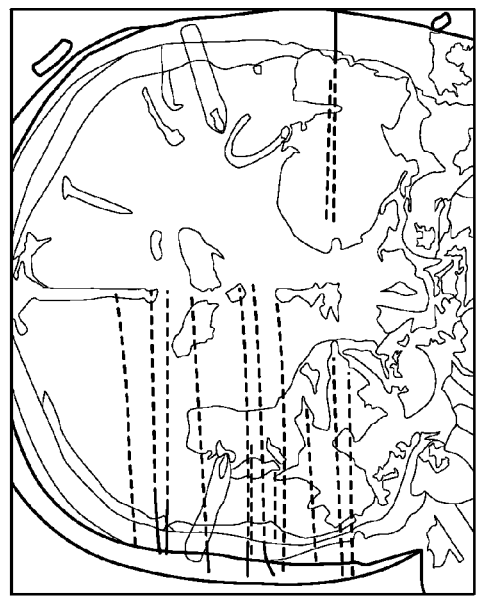

In routine placement of depth electrodes, burr-holes that are each 15 mm in diameter are required for safe visualization of cortical vessels, and therefore only a small number of electrodes are placed. SEEG placement, however, uses several small drill holes (1.8 mm in diameter), allowing many electrodes to be inserted (up to 20). SEEG provides a more complete coverage of the brain, from lateral, intermediate and/or deep structures in a three-dimensional arrangement recorded over hundreds of channels (see FIG. 3D).

Figure 3A:
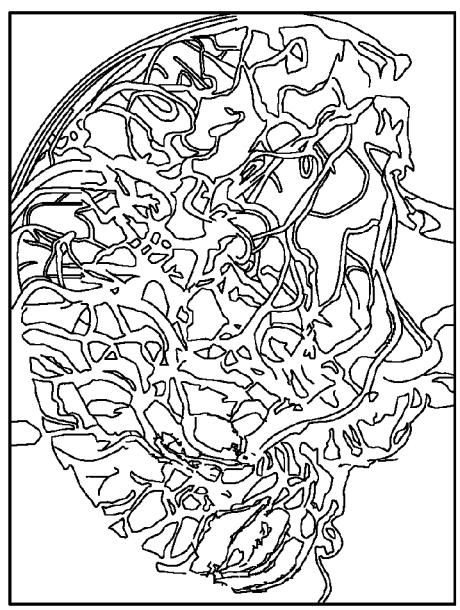
Figure 3C:
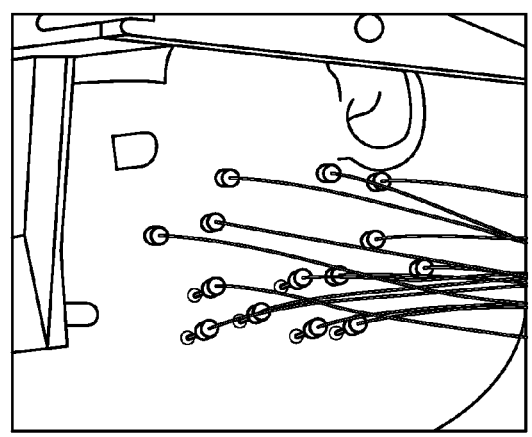

Since direct visualization of the cortical surface is not possible with small drills (FIG. 3C), the SEEG technique requires detailed pre-procedural vascular mapping using pre operative imaging with magnetic resonance angiography (MRA) and cerebral angiography. (FIG. 3A,B). Angiography is an X-ray examination of the blood vessels. The mapping procedure is performed under fluoroscopy using general anesthesia, and an expert neuro-anesthesiologist correctly titrates anesthesia to permit measurement of intracranial EEG. The number and location of implanted electrodes are pre-operatively planned based on a pre-implantation hypothesis, which is formulated in accordance with non-invasive pre-implantation data as seizure semiology, ictal and inter-ictal scalp EEG, MRI images, PET and ictal SPECT scans. Thus, the implantation strategy has the goal of accepting or rejecting the pre-implantation hypothesis of the location of the EZ. During implantation, the surgeon views a 3D overlay of the pre-op image and the angiography (FIG. 3B) and places the electrode in paths that do not intersect any vessels. Using strict technique, this procedure is relatively safe: only 1/1176 implantations last year resulted in an asymptomatic intracranial hemorrhage. Despite the advantages of SEEG over SDE, SEEG recordings are as difficult to analyze as SDE recordings through visual inspection, requiring an assistive tool to help localize the EZ.

EZTrack is a Novel Computational Tool that Employs Sophisticated Algorithms to Process EEG Data.

Another embodiment of the current invention lies in our computational tool—EZTrack. EZTrack can be thought of by viewing the epileptic brain as a dynamic system of interconnected components, or a dynamic network. The implanted electrodes give us observations from this dynamic network, and from these samples we constructed an algorithm that identifies the "bad components" that comprise the EZ. The main idea according to this embodiment is as follows:

For a given snapshot, i.e., a 5 second time window, the EEG signals are modeled by a network graph of nodes connected by weighted edges. Each electrode is considered a node in the graph, and edges between each pair of nodes are weighted by a measured dependency between the two EEG signals in the snapshot (e.g. coherence in a frequency band). See FIG. 4A,B. The graph is equivalently represented by a matrix A, where $A_{ij}$ is the measured dependency between electrodes i and j (FIG. 4C). Then, the "centrality" of electrode i, $C_i$, or the importance of electrode i in the graph is computed directly from the corresponding matrix via eigenvalue decomposition [25]. See below, for details. An electrode will have high centrality if it is either (i) connected to a few electrodes that have high centrality or (ii) if it is connected to several electrodes with low centrality, or both. See FIG. 4D.

EZTrack computes a sequence of graphs as a function of time by sliding the 5 second window every second over all periods before, during, and after seizures. It then computes electrode centralities for each graph over time to generate a "centrality time signal" for each electrode. EZTrack then clusters electrodes according to similar centrality time signals, and the group of electrodes that exhibits a known "EZ centrality signature" is then classified as the epileptic regions while the remaining electrodes are classified as non-epileptic.

We found, in a small cohort of patients, that electrodes spatially closest to the true EZ cluster together and have a characteristic mean centrality signature across all patients with the same seizure types. For example, during partial complex seizures, the mean centrality of the EZ is the lowest near the beginning of seizure and then becomes the largest towards the middle to the end of seizure. Some results for EZTrack examples according to an embodiment of the current invention are described below.

Previous Efforts on EEG Analysis and EZ Localization

Epilepsy has been associated with hypersynchronous behavior in the intracranial recordings [26-28]. Some studies that examined the connectivity of the annotated EZ during inter-ictal periods found these areas to be "locally hypersynchronous" [29-31]. In contrast, other studies found the EZ areas to be less connected during inter-ictal periods [32] or at seizure onset [33, 34].

To reconcile the studies mentioned above, one needs to look at the evolution of connectivity of EZ and non-EZ regions over all time. Early studies looked at the dynamical evolution of intracranial EEG measures during seizures computed from each channel independently (as opposed to network-based measures), such as spectral and wave morphology features [35-38]. However, these measures cannot capture both spatial and temporal correlations. More recently, several studies have looked at the modulation in network connectivity during the course of seizures [39, 40], but without specifically looking for EZ signatures. EZTrack groups together electrodes whose network centrality changes in a similar fashion over all time (non-seizure and seizure periods). It therefore classifies regions based on spatial (network structure) and temporal dynamics in the entire sampled brain and maximizes information contained in the EEG signals.

No prior study has characterized the pathology of both epileptic and non-epileptic planned areas of resection. Standard clinical practice, planned areas of resection are divided into two groups: epileptic (ictal onset zones) and non-epileptic (no ictal patterns) areas, based on the review of the seizure patterns and their anatomical localization(s) extracted from invasive EEG recordings. Invasive monitoring guided resections are rarely restricted to epileptic areas, involving also adjacent non-epileptic cortex, because one cannot definitively classify areas between epileptic electrodes directly adjacent to non-epileptic electrodes. Therefore, resected tissue will typically comprise both Epileptic and non-epileptic regions. One of the few exceptions is when the adjacent non-epileptic areas are located in eloquent brain tissue, which cannot be resected without resulting in permanent neurological deficits.

After surgery, most or all of the resected tissue is sent for histological analysis, where routine stains and immunohistochemical markers against a range of layer-specific, white matter, neural precursor and migratory cell proteins are used to characterize possible pathological substracts associated with epilepsy [50, 56-71]. However, the tissue is not pre-labeled as epileptic and non-epileptic, therefore the pathologies found cannot be traced back to the clinicians' hypothesis of epileptic versus non-epileptic tissue. It may be the case that what clinicians identified as epileptic may be normal and/or the non-epileptic areas may be pathological.

Figure 5:
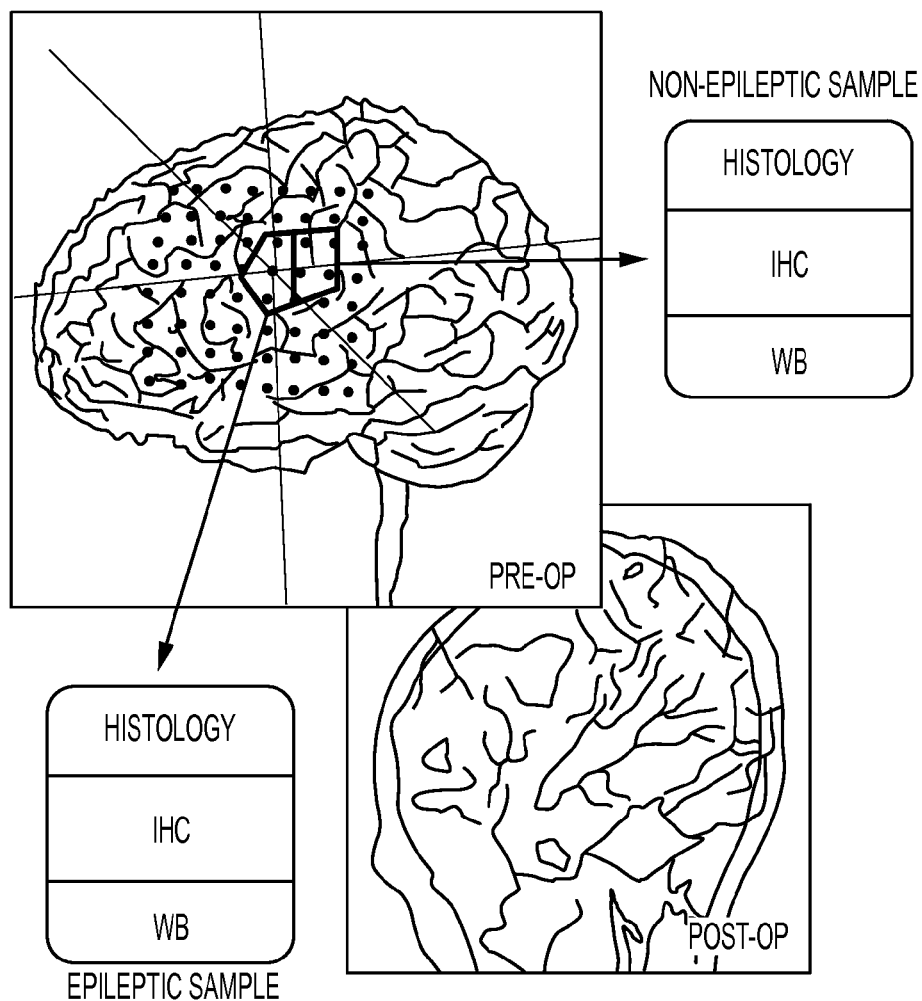
FIG. 5 shows a schematic of histology analysis to be performed separately for Non-Epileptic samples and Epileptic samples.

One can perform specific histological analysis to determine if pathology correlates more specifically to labeled epileptic and non-epileptic specimens. In addition to the standard histological analyses, specimens can also be frozen and preserved for further immunohistochemistry (IHC) and western blotting (WB) analyses (described below), comparing indirect biological markers for in situ epileptogenicity, expected to be highly expressed in epileptic samples in opposed to the non-epileptic ones. See FIG. 5.

To our knowledge, no study has delineated and analyzed separately resected specimens by how they are labeled through the observation of intracranial EEG data. Such a study may determine whether resecting Non-Epileptic areas increases surgical success, and may allow more focal resections thereby minimizing neurological morbidity. It may also allow us to test EZTrack against a more specific measure of "ground truth".

In Summary, Some Embodiments of the Current Invention can Allow One to Perform the Following:

To test a novel computational tool for EZ localization in conjunction with a novel minimally invasive EEG methodology (SEEG). These can be compared to gold standard clinical practice in the US, which is to visually inspect subdural grid EEG ictal and interictal recordings for EZ localization.

To assess pathological markers of tissue identified as epileptic and non-epileptic, which will emphasize, from a histological point of view, the difference between the different cortical areas, ultimately validating the results obtained from the invasive EEG recordings and the analyses obtained from the EZTrack. This specific histological study may provide accurate data to the clinicians that may allow more focal resections thereby minimizing neurological morbidity.

Data Management:

We can collect electrophysiological, clinical, and demographic data for clinical purposes in some applications, which can be analyzed for research purposes. For the electrophysiological data, digital samples of invasive monitoring recordings can be collected, pre-processed (band-pass filtered at 0.5 Hz-10 KHz and digitized at 32 KHz), and later analyzed. The invasive monitoring digital samples can be recorded using Nihon Kohden 1200A EEG diagnostic and monitoring system (Nihon Kohden America, Foothill Ranch, Calif., USA) during the period of extra-operative monitoring at the Epilepsy Monitoring Unit (M60, main campus, Cleveland Clinic). The electrophysiological data can be saved and stored in 2 formats. The first format is the native file format of the EEG system (Nihon Kohden;*.eeg). The second format can be as a MATLAB data file (standard format for analysis). Clinical and demographic data can be stored as text or spreadsheet formats.

Example to Demonstrate Validity of EZTrack in Predicting Surgical Outcome.

In this example, we can use EZTrack to predict whether surgical outcome can be a success or failure for each patient and we can compare these predictions to actual surgical outcomes determined by at least 1 year of follow up clinical visits. A patient's actual surgical outcome is a "success" if he/she is seizure free for at least 1 year post-surgery. The "seizure-free" definition includes patients with seizures restricted to the first postoperative week. In patients who have acute postoperative seizures (APOS) within the first postoperative week, the time to the first recurrence following the APOS will be considered.

Measurements:

We can first use EZTrack to identify the epileptic regions from invasive EEG recordings (see below for details). We can then compare these regions to the EZ identified by clinicians to predict surgical outcome. See arrows (bottom four originating from "Patient Database") in FIG. 6. Finally, we can perform a binary classification test where "condition positive" can be the actual seizure outcome being a success and "condition negative" if the actual outcome is a failure. The "test outcome positive" will be EZTrack's prediction of successful surgical outcome and "test outcome negative" otherwise. EZTrack's predictions of surgical outcomes can be based on invasive EEG recordings. Specifically, if the resected tissue contains all of the regions classified as epileptic by EZTrack, then we would predict a successful surgical outcome; and if the resected tissue does not contain all of the regions labeled as epileptic by EZTrack, then we would predict an unsuccessful surgical outcome. The number of true positives (TP) is the number of instances where the actual outcome is a success and EZTrack's prediction is a success. The number of true negatives (TN) is the number of instances where EZTrack predicts a failure and actual outcome is a failure. We can compute sensitivity [sens=TP/(TP+#actual successes)], and specificity [spec=TN/(TN+#actual failures)] for subpopulations distinguished by invasive EEG method (SEEG vs. SDE implantation). Finally, we can also determine if secondary outcomes, such as reduction in seizure frequency, is correlated with the percentage of epileptic tissue left behind in cases where clinicians did not resect all of EZTrack's epileptic regions; and if neurological morbidity is correlated to the percentage of over-resection in cases where clinicians removed more than EZTrack's epileptic regions. EZTrack may accurately predict successes and failures, and prediction of failures may demonstrate that the tool may be more accurate than visual inspection of invasive EEG by clinicians.

EZTrack has been used to localize the EZ in 10 patients with MRE (5 SEEG, 5 SDE) according to an embodiment of the current invention. Patients and results are summarized in the table in FIG. 9. As shown in FIG. 9, EZTrack correctly predicted the surgical outcome of 9 out of 10 patients. The 5 SEEG patients have been followed up for up to 4-6 months, and the SDE patients have been followed up for at least 1 year. For SEEG patients, EZtrack achieved an overall performance of 88%, sensitivity and 100% specificity, when its predicted EZ was compared to histological reports of resected tissue. For the SDE patients. EZTrack's predictions of the EZ were compared to resected regions (no histology reports available) and it achieved 90% sensitivity and 82% specificity. The latter test assumed that all resected regions have pathological structure, which may not be the case. For an SEEG patient, EZTrack predicted that part of the resected tissue (deemed pathological by clinicians) was normal, which was confirmed by histological analyses.

Seven of the 10 patients' data show consistent centrality signatures during seizure of the "EZ cluster" or EZTrack's epileptic regions, where the cluster's centrality rank increased at seizure onset (indicating it is least connected to the network) and then decreased towards the end of seizure (indicating it is the most connected in the network). See signatures highlighted in FIG. 9. This signature makes sense. At seizure onset, the EEG activity of the EZ suddenly changes and does something different from all the other brain regions, which makes it "disconnected" from the network. Then, through recruitment of other regions, the EZ becomes the "most connected" in the network since all the other signals follow its suit. FIG. 8 shows examples of the computational steps (see below) done by EZTrack.

Finally, a minimum of 2 seizures per patient were used to obtain these results, which translated to an average duration of processing 2.01 hours of EEG recordings. This preliminary data suggests that EZTrack would not only reduce extra-operative monitoring time in the EMU, thereby cutting medical costs and decreasing complications associated with invasive monitoring, but would also decrease localization failures, allowing for more focal resections with less morbidity.

The following describes computational steps according to an embodiment of the current invention:

1) Compute and Rank Network Centrality Over Time:

Network centrality for each node is computed every second using a 5 sec window sliding every second. Specifically, for each window, the brain network is represented by a connectivity matrix [25], As by computing all pairwise total cross-power in the high gamma (50-90 Hz) frequency band, i.e., $$A_{ij} = \int_{50Hz}^{90Hz} P_i(f)P_j(f)df \quad (1)$$

where $P_i$, $P_j$ are the magnitudes of the Fourier transform [72] of the EEG time series in the window recorded from electrodes i, and j respectively. The importance of each electrode to the network connectivity is measured by the strength and number of connections it makes with other electrodes and is referred to as centrality. We used the eigenvector centrality (EVC) to measure the connectivity of each electrode. The EVC of an electrode is defined as the sum of the EVCs of all other electrodes weighted by their edge weights, i.e., $$EVC(i) = \lambda \sum_{j=1}^{N} A_{ij}EVC(j)EVC(i) = \lambda \sum_{j=1}^{N} A_{ij}EVC(j), \quad (2)$$

where $\lambda$ is the leading eigenvalue of A and EVC is the associated eigenvector of A. The leading eigenvectors of connectivity matrices are then calculated numerically at each second during the recordings from the connectivity matrices. Finally, the EVC vector for each second is converted to a ranked vector containing values 1-N, where a 1 was placed in the component of $EVC_{EVC}$ that has the largest centrality and an is placed in the component of EVC that had the smallest centrality.

2) Build Correlation Matrix Based on Rank Evolution Over Time:

The time series of ranks for each electrode i defines a centrality time signal, $x_i(t)$ for i=1, ..., N. $x_{i(t)}^{i-1, ..., N}$ is then smoothed and normalized as follows:

$$\bar{x}_i(t) = \frac{x_i(t) - \langle x_i(t) \rangle}{\|x_i(t) - \langle x_i(t) \rangle\|} \bar{x}_1(t) = \frac{x_{i(t)} - \langle x_i(t) \rangle}{\|x_{i(t)} - \langle x_i(t) \rangle\|}, \quad (3)$$

where $\langle x_i(t) \rangle \langle x_i(t) \rangle$ is the average of the rank signal for electrode i over time and $\|v\|$ is the 2-norm of vector v. EZTrack then computes cross correlations between each $\bar{x}_i(t)^{\bar{x}_i(t)}$ and $\bar{x}_j(t)^{\bar{x}_i(t)\bar{x}_j(t)}$ pair to form a single correlation matrix, C that keeps track of the peak correlations as follows:

$$C_{ij} = \max_t \Sigma_{k=1}^{N} \bar{x}_i(t-k)\bar{x}_j(k), \quad (4)$$

3) Cluster Based on Correlation Matrix:

The electrodes are clustered based on this matrix. In particular, EZTrack reshuffles the rows and columns to generate a new matrix that is approximately block diagonal (we use a graph bi-partition algorithm iteratively to do this), and clusters the electrodes within each block.

Compute Average Rank Signals of Clusters:

Once clusters are identified for each patient, EZTrack computes the average rank signal (un-normalized) for each cluster, i.e, each cluster rank signal is defined as:

$$r_k(t) = \frac{1}{n_k} \sum_{i \in C_k} x_i(t), \quad (5)$$

where $\overline{C}_k$ denotes the set of electrodes in cluster k=1, 2, ..., K, for K clusters.

5) Classify "Epileptic" Electrodes Based on EZ Cluster Signature:

Finally, EZTrack identifies a cluster that exhibits an a priori known signature for the given patient's seizure type. For example, during generalized tonic clonic (seizures, the mean centrality of the EZ is the lowest near the beginning of seizure and then becomes the largest towards the middle to the end of seizure.

We can also model, via linear and logistic regression[49], EZTrack's prediction performance as a function of invasive EEG method, seizure type, EZ location, age etc.

EZTrack according to some embodiments of the current invention has a number of parameters that may be tuned for improvement: (i) The measure of dependency between pairs of EEG signals is currently the cross-power in the gamma frequency band (see eq. (1)). Other frequency bands may be used and/or other dependency measures may be used such as the phase difference in a given frequency band, coherence in a given frequency band, mutual information[72], and peak cross-correlation in time; (ii) The measure of centrality of each electrode is currently the EVC. Other notions of centrality or connectivity may be used such as average degree centrality, closeness centrality, and betweenness centrality etc. [25]; (iii) The method of clustering currently exploits the Kernighan-Lin algorithm for graph partition[25], which finds the best way to split a graph into 2 groups of nodes that are highly connected within each group and weakly connected across the two groups. More general concepts of centrality are intended to be included within the broad concept of the current invention, in addition to fixing it using eigenvector centrality. In addition, we can use other partitioning algorithms such as Fiduccia-Mattheyses algorithm [25] or other clustering methods such as K-means clustering [73], although the latter may not cluster electrodes in a way that maintains homogeneity within cluster defined by centrality rank evolution being similar.

Example to Demonstrate Validity and Efficacy of EZtrack in Patients with a More Specific Measure of Success as Determined by Histology.

Figure 6:
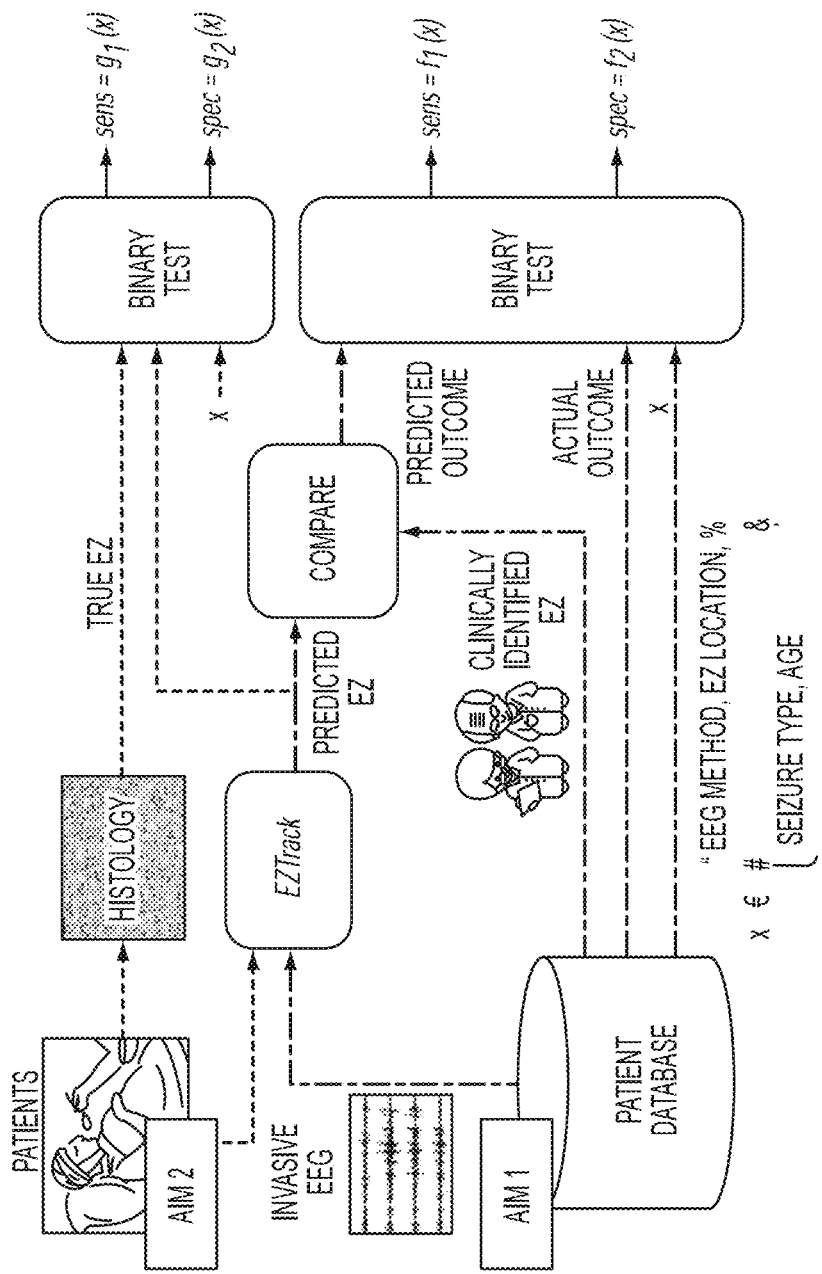
FIG. 6 is a schematic illustration of a Global Study according to an embodiment of the current invention. In Aim 1, EZTrack can predict surgical outcomes of 100 patients in a database, and these predictions can be compared to actual outcomes (lower four arrows). In Aim 2, EZTrack's predictions of the EZ can be compared to True EZ determined by histological analyses on 100 new patients enrolled in this example (top arrows). For each aim, we can model through regression, performance as a function of EEG method, EZ location, seizure type, age etc.
Figure 7A:
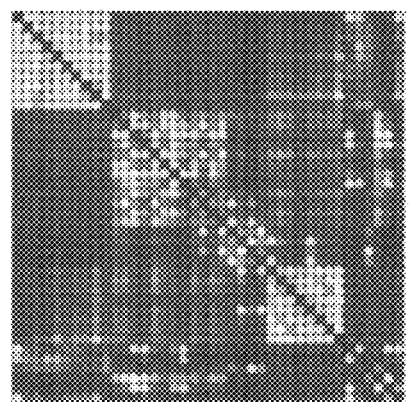
FIGS. 7A-7H show EZTrack Results for SDE Patient (FIGS. 7A-7D) and SEEG Patient (FIGS. 7E-7H). (7A, 7E) Correlation Matrix (C). (7B, 7F) Cluster average centrality time signal. (7C, 7G) Zoom in of cluster average centrality time signals during seizure event with EZ cluster in black. (7D, 7H) EZ cluster shown on image as speckled (7D) and as a solid line (7G) and resected region boxed in red (7D) and shown as diagonal hashed region (7G).
Figure 7B:
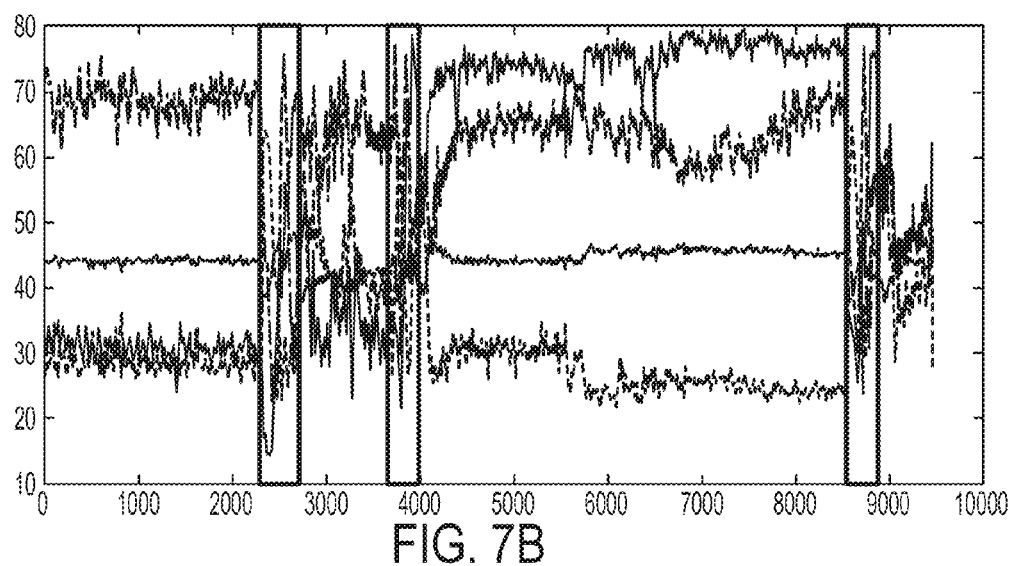
Figure 7C:
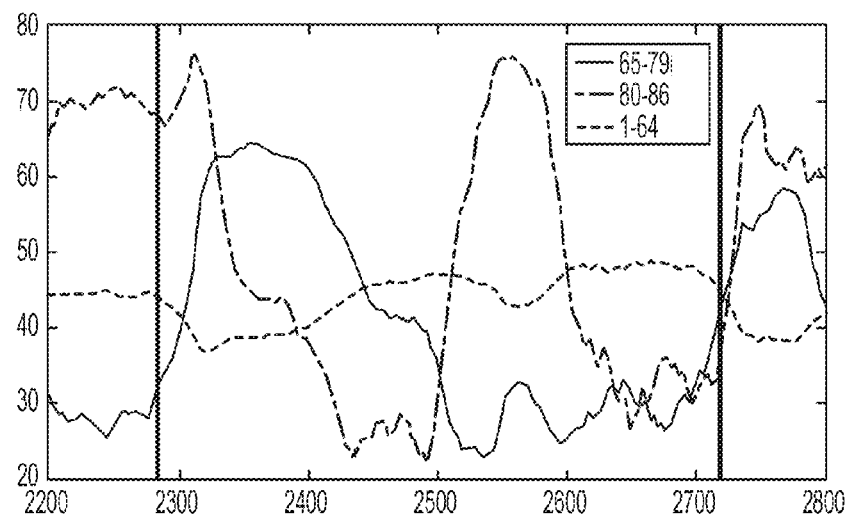
Figure 7D:
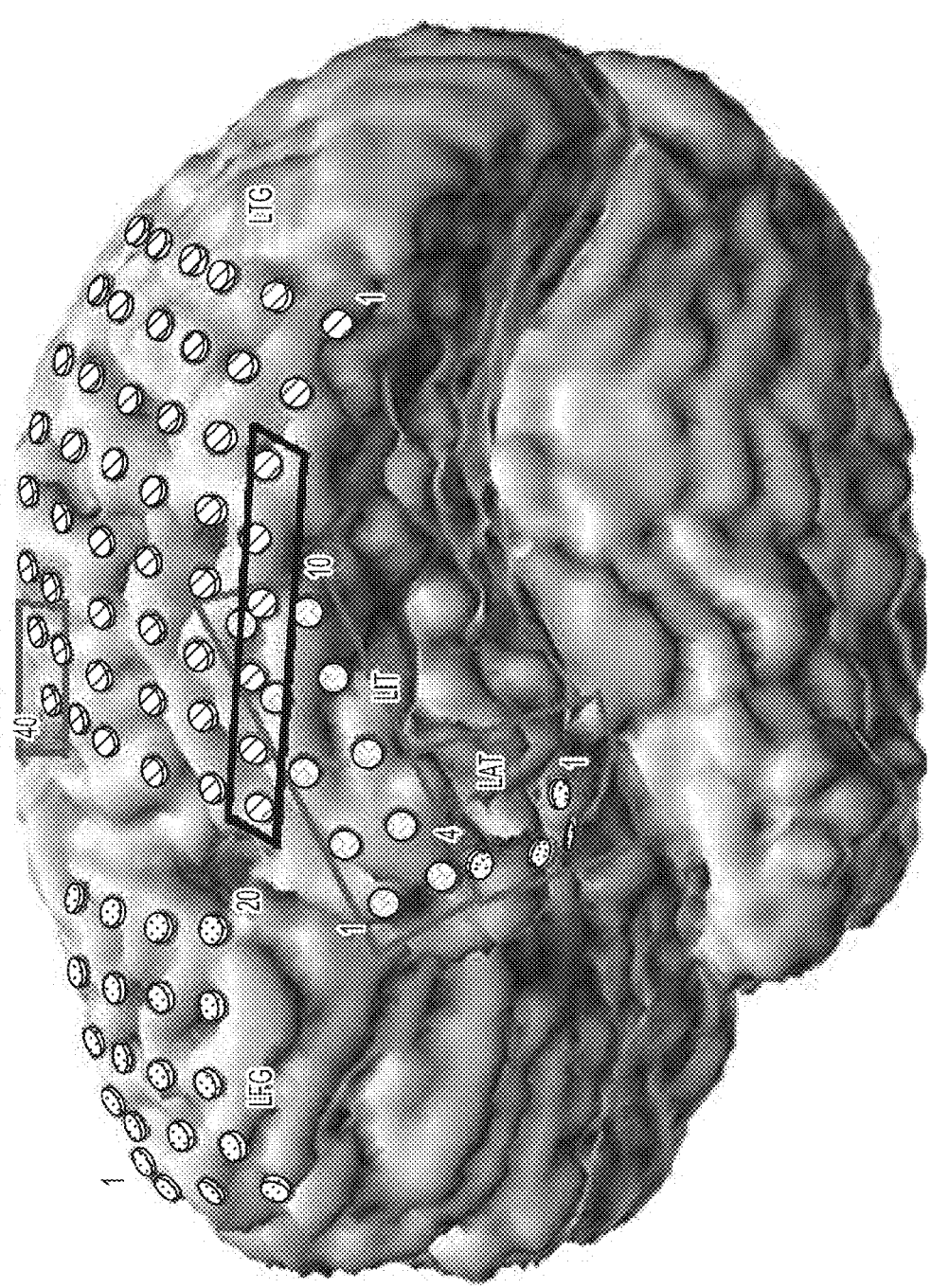
Figure 7E:
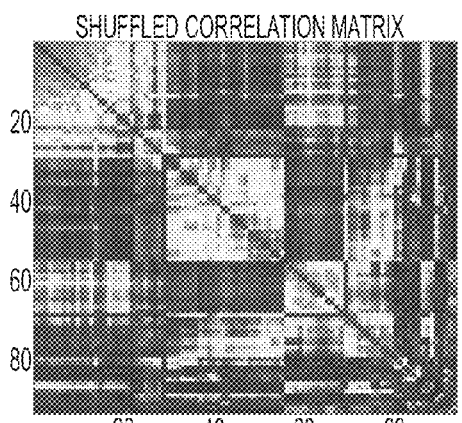
Figure 7F:
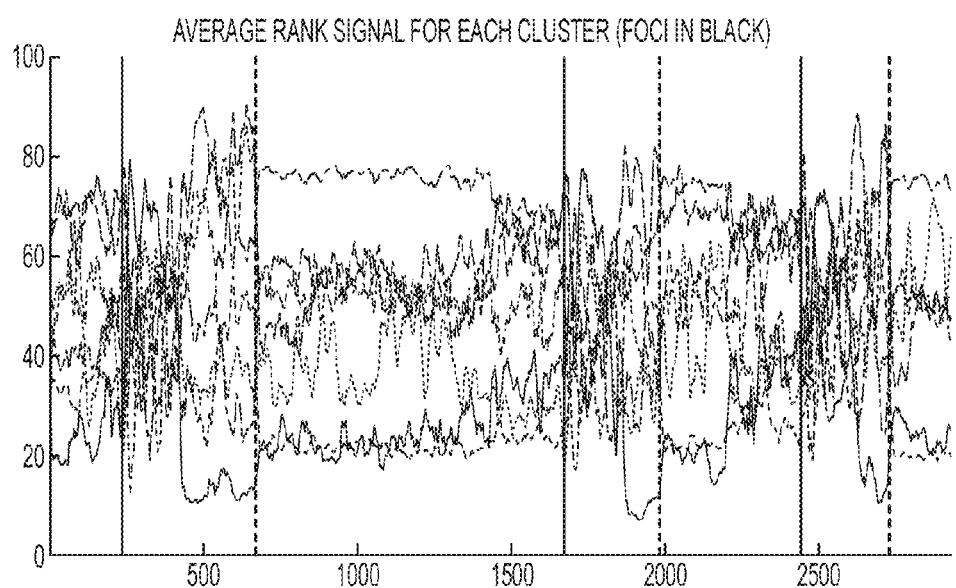
Figure 7G:
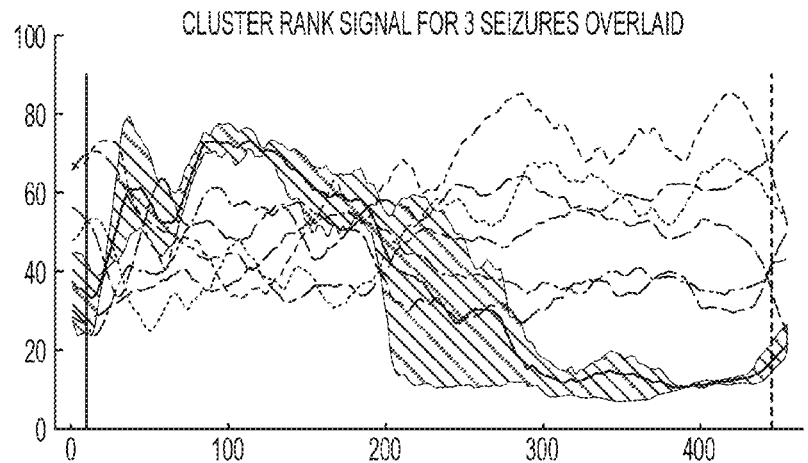
Figure 7H:
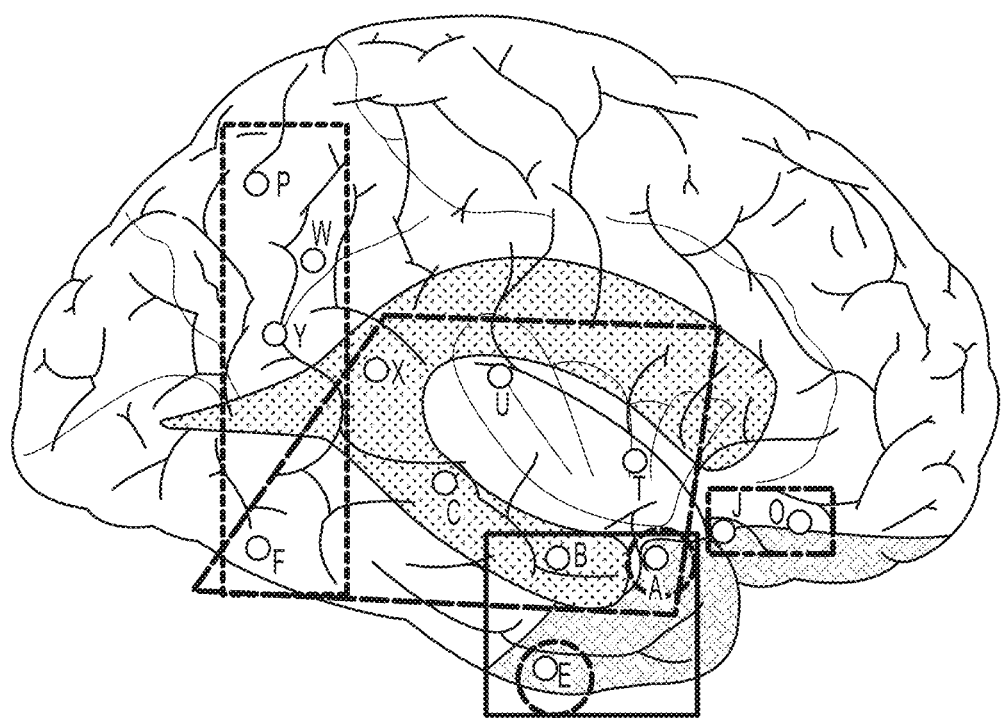
Figure 8A:
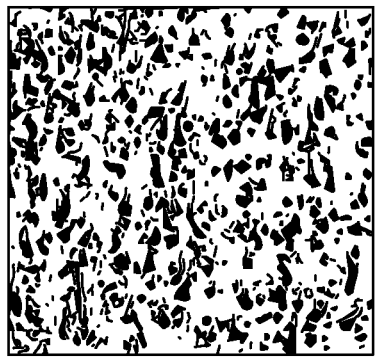
FIGS. 8A-8F show CV and IHC analyses from non-epileptic (left column, A,C,E) and epileptic (right column, B,D,F) samples. A and B show CV staining, demonstrating the normal columnar cortical organization in A and columnar disorganization and presence of dysmorphic and cytomegalic neurons in B. C and D are showing IHC staining with anti-NeuN, confirming normal columnar organization in C and abnormal, disorganized pattern in D. FIGS. E, F, are showing IHC results using anti-NR2B, with higher immunoreactivity in sample F compared to the non-epileptic one (E). Scale bar: 100 μm.
Figure 8B:
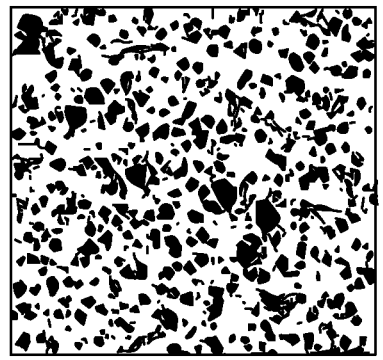
Figure 8C:
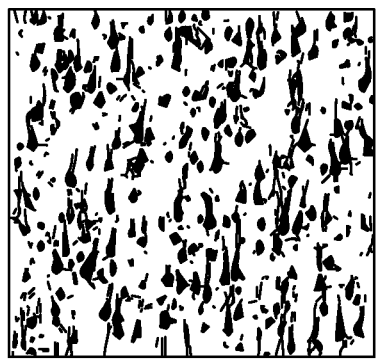
Figure 8D:
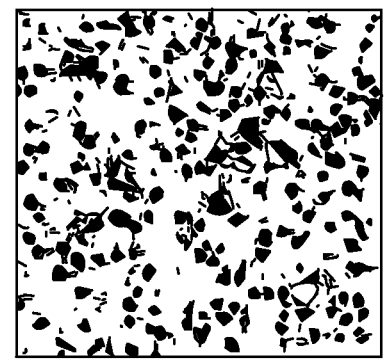
Figure 8E:
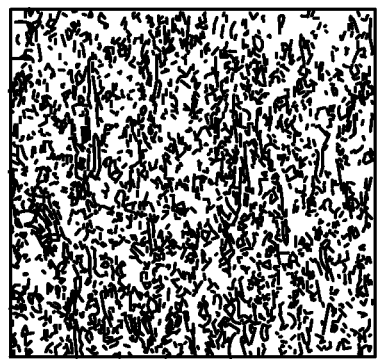
Figure 8F:

The purpose of the human tissue studies is to establish a correlation between the EZTrack's computational analyses and pathological changes associated with MRE, validating the computational results with abnormal histology frequently associated with MRE seizures (arrows (top) in FIG. 6). In addition, molecular histological markers associated with in situ epileptogenicity, as the subunits of the NMDA receptors (NR1 and NR2), can be studied and correlated with the electrophysiological analyses provided by EZtrack, in order to further characterized, now at the molecular level, differential expression of epileptogenicity among the resected samples. The tools of Western blotting (WB) and immunohistochemical staining (IHC) can be used (see below).

(Human tissue characterization by SEEG monitoring) All of the neocortical samples used in the study to test our hypothesis can be from MRE patients who undergo invasive evaluation as part of their presurgical evaluation. We estimate that approximately 40-45 patients can be evaluated using SDE/SEEG methodology per year. The placement and size of the electrodes can be tailored to the size and location of the cortical area(s) to be studied (the decision for the placement and location of the electrodes can be independently made during a multidisciplinary conference meeting). The electrode location can be verified (prior to the resective surgery) using the method of MRI 3D co-registration of T1-weighted MRI and SDE/SEEG post-implantation CT [48]. Video monitoring of the patients' clinical behavior with invasive EEG recordings can be performed for several days in the Epilepsy Monitoring Units (EMU) according to the previously outlined CCF protocol[67].

As previously described [50], the patterns for invasive ictal EEG onset determination can be: 1) paroxysmal fast: duration >10 sec, amplitude >50 µV, frequency >10 Hz, with evolution in amplitude and/or frequency, 2) repetitive spiking: duration >10 sec, amplitude >200 µV, frequency 3-10 Hz, with evolution in amplitude and/or frequency, and 3) paroxysmal fast with repetitive spiking: duration >10 sec, amplitude >50 µV, frequency >10 Hz, intermixed with repetitive spiking and with evolution in amplitude and/or frequency. In parallel, EZTrack may identify anatomical cortical areas with higher/lower propensity for epileptogenic areas. Based on the review of the ictal patterns, EZTrack results and the anatomical localization(s) of the recorded electrode(s), planned areas of resection can be divided into two groups: epileptic and non-epileptic areas. As the resection of the non-epileptic area will not be done for the sole purpose of acquiring a control sample for the proposed experiments but as part of an anatomical resection, there will be instances when non-epileptic areas will not be resected and therefore the patient can be eliminated from the study (because of the lack of internal pair-matched control).

(Tissue collection and processing) After exposure of the brain during surgery, the location of electrodes within the pre-planned resection area can be marked using sterile brilliant green ink (using MRI-reconstructed images digitally fused with previous post-implantation CT). There will be no tissue resected for the sole purpose of the performance of the proposed experiments. The resected specimens are given to a trained technician immediately after en bloc removal by the neurosurgeon. Based on our previous experience in performing the same type of tissue harvesting, we estimate that the typical size of each EEG-characterized area will vary between 1 and 2 $cm^3$. Each characterized region (A: epileptic and B: non epileptic) will be divided into 3 blocks through cutting in the coronal plane: 1) block 1 for standard surgical pathology analyses (paraffin embedded), 2) block 2 for morphological and immunohistochemical studies (saved in paraformaldehyde and processed as below), and 3) block 3 for protein assays (fresh frozen on dry ice). The methods in the design to carry out Example 2 have already been established by Gonzalez-Martinez [52, 54, 56].

Measurements:

All tissue blocks that were previously saved in paraformaldehyde (fresh from operating room or after in vitro studies) can be sequentially sectioned at 30 µm each and saved in cryoprotectant solution till further staining We estimate that the thickness of each section will be between 2-5 mm, therefore 60-150 (30 µm) sections can be recovered from each block. The measurements that can be performed are detailed below.

After histological analyses, we may demonstrate the validity and accuracy of EZtrack in identifying the EZ with a more specific measure of success as determined by histology. We can perform a binary classification test wherein "condition positive" is the set of brain regions determined to exhibit pathological connectivity and structural changes in the resected tissue, and "condition negative" can be the brain regions determined to have normal structure. The "test outcome positive" can be the set of brain regions EZTrack classifies as epileptic, and "test outcome negative" can be the brain regions EZTrack classifies as non-epileptic. We can then compute sensitivity, and specificity for all patients; and we can also model, via linear and logistic regression, a)

EZTrack's performance (sens,spec), b) post-surgery seizure frequency, c) post surgery rate of adverse events including depression and memory impairment, as a function of invasive EEG method.

Further Examples

We have been able to study the correlation between pathological findings and in situ epileptogenicity in resected human brain cortex from MRE patients using a multidisciplinary approach that involves close collaboration between clinical neurophysiologists, neurosurgeons, neuropathologists, neuroradiologists, and neuroscientists [69, 70, 71, 64, 58]. This approach has permitted: 1) The correlation of MRI data (FLAIR signal co-registered on T1-weighted 3D reconstruction) with invasive EEG recordings (both intraoperative and extraoperative) in dysplastic and surrounding tissue, and 2) histological/ICC characterization with direct correlations between those pathological changes and in situ electrical activities in carefully identified and resected neocortical specimens. More specifically, we were able to conclude that there is a clear correlation between NR1 and NR2B immunopositive resected specimens with in situ epileptogenicity, defined by intracranial invasive monitoring [54, 70]. (FIG. 8).

Statistical Analyses and Power Considerations:

Estimates of the number of samples and patients needed to perform human tissue studies: These estimates are based on our experience in screening patients and performing morphological studies on resected tissue. A Wilcoxon-Rank-Sum test was used to estimate the number of samples needed. For a power of 0.8, significance of 0.05, odds probability of sample A>sample B is 0.80, with a ratio of sample B over sample A is 1, the sample size needed for each group is 15. Sample A refers to epileptic samples and B refers to non-epileptic samples. Therefore, we estimate that we will need 15-20 pair-matched samples to perform the proposed human studies. Since not all patients screened for the study will be included, we estimate that only 20% of these patients satisfy all the criteria (patients with focal cortical epilepsy who undergo SDE or SEEG and we would be able to acquire epileptic and non-epileptic samples. Therefore, based on the estimated number of SDE/SEEG cases of ~40 per year, we estimate that we will need two years to acquire the desired sample size of 15-20 pair-matched epileptic and non-epileptic samples.

We expect a clear and consistent difference between epileptic and non-epileptic samples: epileptic samples, as defined by EZTrack, will demonstrate pathological changes as different types of CD, frequently associated with in situ epileptogenicity. In contrast, non-epileptic samples will demonstrate normal pathology. In a similar way, ICH analyses will demonstrate a qualitative difference in the expression of NR1, NR2 and NR2B. Lastly, the WB will demonstrate, from a quantitative aspect, the difference in the expression of the studied proteins in the epileptic and non-epileptic samples. It is well established that the presence of pathological changes in post-resection specimens is a predictor variable for sustained seizure freedom after surgery [41, 56, 57].

Among different pathological substrates malformations of cortical development (MCD) are the most common finding in neocortical MRE, having well described intrinsic epileptogenicity features [51]. MCDs are a large group of lesions with distinct histological, EEG, clinical, and imaging features [65, 68, 66]. EEG techniques have been considered as the most important tool for the identification of the EZ as the majority of patients with MCDs (between 85 and 100%) show epileptiform discharges on their interictal scalp EEG recordings, as the expression of their intrinsic epileptogenicity [41]. To date, studies have focused on the EEG findings but failed to make direct correlations between the in situ electrical characteristics and the pathological findings in the resected cortex.

Conclusions

This study can provide the first set of data that may establish a highly innovative EZ localization tool (EZTrack) and a minimally invasive electrode implantation (SEEG) used for pre-surgical evaluation of MRE patients. These two aspects are currently not available in the US and therefore must be compared to the US's gold standard in a scientific and statistically sound manner before widespread use. Widespread usage of EZTrack and SEEG may provide new methods of pre-surgical evaluation to better personalize treatment for each MRE patients. More targeted treatment may reduce pre-surgical evaluation time, morbidity and mortality rates, and surgery failures for a large patient population worldwide that to date has no alternative treatment.

Details of Histological Experiments and Measurements

1. Cresylecht Violet (CV) staining can be performed on all samples in the study. The purpose is to confirm (or not) the pathological diagnosis. Microscopic examination of the sections can be done by a blinded neuropathologist (co-investigator Prayson).

Single Immunohistochemical (IHC) Labeling:

Antibodies against the following proteins will be used: NR1 (mouse, Pharmingen), NR2 (rabbit, Chemicon), NR2B (rabbit, Chemicon) and NeuN (Rat, Chemicon). The purpose is to characterize and map in situ changes in samples that showed distinct electrical patterns from EEG recordings. We will perform semi-quantitative analyses of IHC staining We will use visual assessment of the various immunoreactive densities and statistically compare them between EZTrack-defined epileptic and non-epileptic tissues. These methods are routinely employed in our lab [56, 60, 70] and utilized in other labs [59, 62]. Briefly, two skilled observers (PI and Prayson) will independently and blindly classify the darkness of the staining using an ordinal scale and the observers' scores will be averaged into a final ordinal value. Differences between epileptic and non-epileptic tissues will be statistically analyzed. IHC on human tissue will be conducted as previously described [56, 60, 70, 71]. The fixed tissue blocks will be cryoprotected overnight in 20% buffered sucrose. The blocks will be frozen quickly in crushed dry ice and cut into 30 μm sections on a cryostat (Leica 1850 CM, Heidelberg, Germany). 0.05 M TBS (pH 7.6) will be used as the rinsing buffer throughout the IHC staining procedure on free-floating sections with rinses between each step: 5 min in 3% hydrogen peroxide/10% methanol in TBS; 60 min in a blocking solution of 1.5% normal serum in TBS; 18 h overnight in primary antibody diluted in TBS containing 1% normal serum; 35 min in biotinylated secondary antibody. To visualize the immunoreactivity, the sections will be reacted for 7 min in 0.05% 3,3'-diaminobenzidine tetrahydrochloride and 0.01% H2O2 in TBS. The reaction will be terminated through transfer of the sections to ice-cold TBS.

Western Blotting (WB) Studies:

In order to semi-quantify the total NR1, NR2 and NR2B protein volume differences between the epileptic and non-epileptic samples, we will performe WB on the tissue adjacent to that used for IHC and CV staining Antibodies against NR1, NR2 and NR2B will be used. The brain tissues will be homogenized in 1 ml ice-cold 0.32 M mannitol containing 1 mM EDTA (pH 7.4) and centrifuged at 1000 g for 10 min at 4° C. The resulting pellet will be re-suspended in 1 ml of re-suspension buffer (100 mM PBS, pH 7.45, 5 mM Tris-HCl, 1 mM MgSO4, 0.5 mM EDTA, 1% glycerol). Protein concentrations will be determined by the Bio-Rad DC protein assay using bovine serum albumin as the standard. The membrane extract will subjected to 4-20% linear gradient SDS-PAGE and transferred to nitrocellulose membrane by electroblotting. Blots will be blocked with 2.5% non-fat milk in PBS buffer and then incubated with primary antibody overnight at 4° C. After the primary antibody incubation, membranes will be washed and incubated with peroxidase-conjugated secondary antibody and developed with ECL (Amersham, Arlington Heights, Ill.). The transferred blotted membrane will be stained with Ponceau-S to verify that each lane is loaded with equivalent amounts of protein. The development will be done on Kodak X-OMAT film. Densitometry of the immunoblots will be used to quantify the differences in expression of each protein level. The blots will be scanned by a 36-bit flat bed scanner (Arcus II), and the digital images containing the gel bands will be imported into a computer densitometry program (NIH Image v.1.58, public domain). The digitized gray values of each band will then be imported into Microsoft Excel. Statistical comparisons of the different protein densities in the epileptic and non-epileptic tissues will be made.

REFERENCES AND LINKS

1. Brodie, M. J., Shorvon, S. D., Canger, R. et al. Commission on European Affairs: appropriate standards of epilepsy care across Europe. Epilepsia 1997; 28:1245-1250.
2. Berg A T, Kelly M M. Defining intractability: comparisons among published definitions. Epilepsia. 2006 February; 47(2):431-6.
3. Kwan P, Brodie M J. Early identification of refractory epilepsy. N Engl J Med. 2000 Feb. 3; 342(5):314-9.
4. Berg, A T. Identification of Pharmacoresistant Epilepsy. Neurol Clin 27 (2009) 1003-1013.
5. Murray M I, Halpern M T, Leppik I E. Cost of refractory epilepsy in adults in the USA. Epilepsy Research. 1996; 23:139-148.
6. Begley C E, Famulari M, Annegers J F, Lairson D R, Reynolds T F, Coan S, Dubinsky S, Newmark M E, Leibson C, So E L, Rocca W A. The cost of epilepsy in the United States: an estimate from population-based clinical and survey data. Epilepsia 2000; 41: 342-351.
7. Ferro, M A, Speechley K N. Depressive symptoms among mothers of children with epilepsy:
8. Schuele S U, Lüders H O. Intractable epilepsy: management and therapeutic alternatives. Lancet Neurol. 2008 June; 7(6):514-24.
9. Hermann B P, Seidenberg M, Dow C, Jones J, Rutecki P, Bhattacharya A, Bell B. Cognitive prognosis in chronic temporal lobe epilepsy. Ann Neurol. 2006 July; 60(1):80-7.
10. Gilliam F G, Kuzniecky R, Meador K. Patient-oriented outcome assessment after temporal lobectomy for refractory epilepsy. Neurology 1999; 53:687-94.
11. Gilliam F G. Diagnosis and treatment of mood disorders in persons with epilepsy. Curr Opin Neurol. 2005 April; 18(2):129-33.
12. Lüders H O, Najm I, Nair D, Widdess-Walsh P, Bingman W. The epileptogenic zone: general principles. Epileptic Disord. 2006 August; 8 Suppl 2:S1-9. Erratum in: Epileptic Disord. 2008 June; 10(2):191.
13. McIntosh A M, Kalnins R M, Mitchell L A, Fabinyi G C, Briellmann R S, Berkovic S F. Temporal lobectomy: long-term seizure outcome, late recurrence and risks for seizure recurrence. Brain. 2004 September; 127(Pt 9):2018-30. Epub 2004 Jun. 23.
14. Jeha L E, Najm I M, Bingaman W E, Khandwala F, Widdess-Walsh P, Morris H H, Dinner D S, Nair D, Foldvary-Schaeffer N, Prayson R A, Comair Y, O'Brien R, Bulacio J, Gupta A, Liiders H O. Predictors of outcome after temporal lobectomy for the treatment of intractable epilepsy. Neurology. 2006 Jun. 27; 66(12):1938-40.
15. Jeha L E, Najm I, Bingaman W, Dinner D, Widdess-Walsh P. Surgical outcome and prognostic factors of frontal lobe epilepsy surgery. Brain (2007); 130:574-584.
16. Urbacj H, Hattinggen J, von Oertzen, et al, M R imaging in the presurgical workup of patients with drug-resistant epilepsy, AJNR 25:919-926 June/July 2004
17. Crandall P H. Role of neurosurgery in management of medication-resistant epilepsy. In Plan for Nationwide Action on Epilepsy. Vol 2, Part 2. Pub. No. NIH 78-277. Washington D.C., US Gov. Printing Office, 1977: 327-334.
18. Widdess-Walsh P, Jeha L, Nair D, Kotagal P, Bingaman W, Najm I. Subdural electrode analysis in focal cortical dysplasia: predictors of surgical outcome. Neurology. 2007 Aug. 14; 69(7):660-7.
19. Jung, Won Young; Pacia, Steven V.*; Devinsky, Orrin* (1999) Neocortical Temporal Lobe Epilepsy: Intracranial EEG Features and Surgical Outcome. Journal of Clinical Neurophysiology: September 1999—Volume 16—Issue 5—p 419.
20. Ernst Niedermeyer, Fernando Lopes da Silva (2004) Electroencephalography: Basic Principles, Clinical Applications, and Related Fields. Lippincott Williams & Wilkins; Fifth edition.
21. Santaniello S, Burns S P, Golby J, Singer J, Anderson W S, Sarma S V. (2011) Quickest Detection of Seizure Onsets in Drug-Resistant Patients: An Optimal Control Approach. Epilepsy & Behavior, 22, pp 49-60.
22. Kerr M, Burns S, Gale J, Sarma S V (2011) Multivariate Analysis of SEEG Signals During Seizure. Proceedings of the 33rd IEEE EMBS Conference.
23. Yaffe R, Burns S, Gale J, Park H J, Bulacio J, Gonzalez-Martinez J, Sarma S V. Brain State Evolution During Seizure and under Anesthesia: A Network-Based Analysis of Stereotaxic EEG Activity in Drug-Resistant Epilepsy Patients. Proceedings of the 34th IEEE EMBS Conference.
24. Heinz Gregor Wieser. Epilepsy surgery: past, present and future. Seizure: European Journal of Epilepsy. Volume 7, Issue 3, Pages 173-184, June 1998.
25. Newman M J (2010) Networks: An Introduction. 720 pgs. Oxford University Press, USA.
26. Penfield W, Jasper H H (1954) Epilepsy and the functional anatomy of the human brain. Boston: Little Brown.
27. Ponten S C, Bartolomei F, Stam C J (2007) Small-world networks and epilepsy: Graph theoretical analysis of intracerebrally recorded mesial temporal lobe seizures. Clin. Neurophys., 118:918-927.
28. Baier G, Muller M, Stephani U, Muhle H (2007) Characterizing correlation changes of complex pattern transitions: The case of epileptic activity. Phys. Let. A, 363:290-296.
29. Schevon C A, Cappell J, Emerson R, Isler J, Grieve P, Goodman R, Mckhann G, Weiner H, Doyle W, Kuzniecky R, Devinsky O, Gilliam F (2007) Cortical abnormalities in epilepsy revealed by local EEG synchrony. NeuroImage, 35:140:148.
30. Zaveri H P, Pincus S M, Goncharva I I, Duckrow R B, Spencer D D, Spencer S S (2009) Localization-related epilepsy exhibits significant connectivity away from the seizure-onset area. NeuroReport, 20:891-895.
31. Andrzejak R G, Chicharro D, Lehnertz K, Mormann F (2011) Using bivariate signal analysis to characterize the epileptic focus: The benefit of surrogates. Phys. Rev. E, 83:046203.

32. Warren C P, Hu S, Stead M, Brinkmann B H, Bower M R, Worrell G A (2010) Synchrony in normal and focal epileptic brain: the seizure onset zone is functionally disconnected. J. Neurophysiol., 104:3530-3539.
33. Netoff T I, Schiff S J (2002) Decreased Neuronal Synchronization during Experimental Seizures. J Neurosci., 22(16):7297-7307.
34. Kramer M A, Kolaczyk E D, Kirsch H E (2008) Emergent network topology at seizure onset in humans. Epilepsy Res., 79:173-186.
35. Wendling F, Bellanger J J, Badier J M, Coatrieux J L (1996) Extraction of spatiotemporal signatures from depth EEG seizure signals based on objective matching in warped vectorial observations. IEEE Trans. Biomed. Eng., 43(10):990-1000.
36. Wu L, Gotman J (1998) Segmentation and classification of EEG during epileptic seizures. Electroenceph. Clin. Neurophys., 106:344-356.
37. Schiff S J, Sauer T, Kumar R, Weinstein S L (2005) Neuronal spatiotemporal pattern discrimination: The dynamical evolution of seizures. NeuroImage, 28:1043-1055.
38. Arthuis M, Valton L, Regis J, Chauvel P, Wendling F, Naccache L, Bernard C, Bartolomei F (2009) Impaired consciousness during temporal lobe seizures is related to increased long-distance cortical-subcortical synchronization. Brain, 132:2091:2101.
39. Schindler K A, Bialonski S, Horstmann M T, Elger C E, Lehnertz K (2008) Evolving functional network properties and synchronizability during human epileptic seizures. Chaos, 18:033119.
40. Kramer M A, Eden U T, Kolaczyk E D, Zepeda R, Eskandar E N, Cash S S (2010) Coalescence and fragmentation of cortical networks during focal seizures. J. Neurosci., 30(30):10076-10085.
41. Bulacio J, Jehi L, Wong C, Gonzalez-Martinez J, Kotagal P, Nair D, Najm I, Bingaman W. Long-term seizure outcome after resective surgery in patients evaluated with intracranial electrodes. Epilepsia. 2012.
42. Risinger M, Gumnit R. (1995) Intracranial electrophysiologic studies. Neu-roimaging Clin N Am 5:559-573.
43. Najm I, Bingaman W, Lüders H. (2002) The use of subdural grids in the management of focal malformations due to abnormal cortical develop-ment. Neurosurg Clin N Am 13:87-92.
44. Bancaud J, Angelergues R, Bernouilli C, Bonis A, Bordas-Ferrer M, Bres-son M, Buser P, Covello L, Morel P, Szikla G, Takeda A, Talairach J. (1970) Functional stereotaxic exploration (SEEG) of epilepsy. Electro-encephalogr Clin Neurophysiol 28:85-86.
45. Kahane P, Minotti L, Hoffmann D, Lachaux J P, Ryvlin P. (2004) Invasive EEG in the definition of the seizure onset zone: depth electrodes. In: Rosenow F, Lüders H (Eds) Presurgical assessment of the epilepsies with clinical neurophysiology and functional imaging. Elsevier, Amsterdam, the Netherlands, pp. 109-133.
46. Nair D R, Burgess R, McIntyre C C, Lüders H. (2008) Chronic subdural electrodes in the management of epilepsy. Clin Neurophysiol 119: 11-28.
47. Onal C, Otsubo H, Araki T, Chitoku S, Ochi A, Weiss S, Elliott I, Snead O C, Rutka J T, Logan W. (2003) Complications of invasive subdural grid monitoring in children with epilepsy. J Neurosurg 98:1017-1026.
48. Gonzalez-Martinez, J, Bulacio J, Alexopolous A, Jehi L, Bingaman W, Najm I. Stereoelectroencephalography in the "difficult to localize" refractory focal epilepsy: Early Experience form a North American Epilepsy Center. Epilepsia (accepted for publication).
49. Cohen, J., Cohen P., West, S. G., & Aiken, L. S. (2003). Applied multiple regression/correlation analysis for the behavioral sciences. (2nd ed.) Hillsdale, N.J.: Lawrence Erlbaum Associates
50. Boonyapisit K, Najm I, Klem G, Ying Z, Burrier C, LaPresto E, Nair D, Bingaman W, Prayson R, Luders H. (2003) Epileptogenicity of focal malformations due to abnormal cortical development: direct electrocorticographic-histopathologic correlations. Epilepsia. 44(1):69-76.
51. Engel, J. et al., 1990. Presurgical evaluation for partial epilepsy: relative contributions of chronic depth-electrode recordings versus FDG-PET and scalp-sphenoidal ictal EEG. Neurology, 40(11), pp. 1670-1677.
52. González-Martinez J A, Ying Z, Prayson R, Bingaman W, Najm I. Glutamate Clearence mechanisms in resected cortical dysplasia. J Neurosurg. 2011 Nov. 12.
53. Gonzalez-Martinez J A, Hugher G, Chen T, Bulacio J, So N, Bingaman W, Jehi, L, Hantus S, Najm I. Invasive monitoring using depth electrodes at a Noth American Center: A prospective study analyzing the feasibility and safety of stereoelectroencephalography (SEEG) in the diagnosis and treatment of intractable epilepsy. Epilepsia 2010 AES abstracts.
54. Gonzalez-Martinez J A, Möddel G, Ying Z, Prayson R A, Bingaman W E, Najm I M. Neuronal nitric oxide synthase expression in resected epileptic dysplastic neocortex. J Neurosurg. 2009 February; 110(2):343-9.
55. González-Martinez J A, Srikijvilaikul T, Nair D, Bingaman W. Long-term seizure outcome in reoperation after failure of epilepsy surgery. Neurosurgery. 2007 May; 60(5):873-80; discussion 873-80.
56. Gonzalez-Martinez J, Bingaman W, Steven T, Najm I. Neurogenesis in the postnatal human epileptic brain. J Neurosurg. 2007 September; 107(3):628-35.
57. Jeha, L E et al., 2006. Predictors of outcome after temporal lobectomy for the treatment of intractable epilepsy. Neurology, 66(12), pp. 1938-1940.
58. Kellinghaus C, Moddel G, Shigeto H, Ying Z, Jacobsson B, Gonzalez-Martinez J, Burrie C, Janigro D, Najm I. Dissociation between in vitro and in vivo epileptogenicity in a rat model of cortical dysplasia. Epileptic Disord. 2007 March; 9(1):11-9. Epub 2007 Feb. 15.
59. Kerfoot C, Vinters H, Mathern G (1999) Cerebral cortical dysplasia: giant neurons show potential for increased excitation and axonal plasticity. Dev. Neurosci 21: 260-270.
60. Najm I, Ying Z, Babb T, Mohamed A, LaPresto E, Wyllie E, Kotagal P, Bingaman W, Foldvary N, Morris H, Liiders H. NMDA receptor 2A/B subtype differential expression in human cortical dysplasia: Correlation with in situ epileptogenicity. Epilepsia 2000; 41:971-976.
61. Najm I, Ying Z, Boonyapisit K, Bingaman W, Prayson R, Liiders H. Malformations due to abnormal cortical development: Expression and mechanisms of epileptogenicity. Advances in Clinical Neurophysiology, 2002, 54:462-469.
62. Mathern G W, Babb T L, Pretorius J K (1995) Reactive synaptogenesis and neuron densities for neuropeptide Y, somatostatin, and glutamate decarboxylase immunoreactivity in the epileptogenic human fasciadentata. J Neurosci 15:3990-4004.
63. Mikuni N, Babb T L, Ying Z, Najm I, Nishiyama K, Wylie C, Yacubova K, Okamoto T, Bingaman W (1999) NMDA-receptor 1 and 2A/B coassembly increased in human epileptic focal cortical dysplasia. Epilepsia 40: 1683-1687.

64. Moddel G, Jacobson B, Ying Z, Janigro D, Bingaman W, Gonzalez-Martinez J, Kellinghaus C, Prayson R, Najm I. NR2B-subunit specific NMDA receptor inhibition by ifenprodil differentially suppresses epileptiform field potentials in dysplastic human neocortex. Brain Res. 2005 Jun. 7; 1046(1-2):10-23.

65. Palmini A, Gambardella A, Andermann F, Dubeau F, da Costa J C, Olivier A, Tampieri D, Gloor P, Quesney F, Andermann E. (1995) Intrinsic epileptogenicity of human dysplastic cortex as suggested by corticography and surgical results. Ann Neurol 37: 476-487.

66. Prayson R A, Estes M L (1995) Cortical dysplasia: a histopathologic study of 52 cases of partial lobectomy in patients with epilepsy. Hum Pathol. 26(5):493-500.

67. Rosenow F, Luders H. Pre-surgical evaluation of epilepsy. Brain 2001; 124 (Pt 9):1683-700.

68. Taylor, D C, Falconer, M A, Bruton, C J, Corsellis J A (1997) Focal dysplasia of the cerebral cortex in epilepsy. J. Neurol Neurosurg Psychiatry. 34: 369-387.

69. Ying Z, Gonzalez-Martinez J, Bingaman W, Najm I. Expression of Neuronal Stem Cell Surface Marker CD133 in balloon cells of human focal cortical dysplasia. Epilepsia. 2005 November; 46(11):1716-23.

70. Ying Z, Babb T L, Mikuni N, Najm I, Drazba J, Bingaman W. Selective co-expressions of NMDAR2A/B and NMDAR1 subunit proteins in dysplastic neurons of human epileptic cortex. Experimental Neurology, 159: 409-418, 1999

71. Ying Z, Babb T L, Comair Y G, Bingaman W, Bushey M, Touhalisky K (1998) Induced expression of NMDAR2 proteins and differential expression of NMDAR1 splice variants in dysplastic neurons of human epileptic neocortex. J Neuropath Exp Neurol 57:47-62.

72. Bendat J S, Piersol A G (1986) Random Data: Analysis and Measurement Procedures, 2nd edition, John Wiley & Sons: New York, N.Y.

73. MacQueen, J. B. (1967). Some Methods for classification and Analysis of Multivariate Observations. Proceedings of 5th Berkeley Symposium on Mathematical Statistics and Probability. University of California Press. pp. 281-297

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of identifying an epileptogenic zone of a subject's brain, comprising:
   receiving a plurality of electrical signals from a corresponding plurality of surgically implanted electrodes;
   calculating a first plurality of connectivities between each pair of electrodes based on a portion of each of said plurality of electrical signals corresponding to a first time period;
   assigning a rank corresponding to each electrode for said first period of time based on said first plurality of connectivities to provide a first plurality of ranks;
   calculating a second plurality of connectivities between each pair of electrodes based on a portion of each of said plurality of electrical signals corresponding to a second time period;
   assigning a rank corresponding to each electrode for said second period of time based on said second plurality of connectivities to provide a second plurality of ranks;
   identifying a cluster of electrodes among said plurality of electrodes based on relative changes between said first plurality of ranks from said first time period and said second plurality of ranks at said second time period;
   identifying said epileptogenic zone based on said cluster of electrodes; and
   displaying said identified epileptogenic zone.

2. A method of identifying an epileptogenic zone of a subject's brain according to claim 1, wherein said calculating said first plurality of connectivities calculates a connectivity matrix by using the formula $$A_{ij} = \int_{50Hz}^{90Hz} P_i(f)P_j(f)df$$

where $P_i$, $P_j$ are magnitudes of Fourier transforms of said portion of said electrical signal corresponding to said first time period from electrodes i, and respectively, of said plurality of electrodes.

3. A method of identifying an epileptogenic zone of a subject's brain according to claim 2, wherein said calculating said second plurality of connectivities calculates a connectivity matrix by using the formula $$A_{ij} = \int_{50Hz}^{90Hz} P_i(f)P_j(f)df$$

where $P_i$, $P_j$ are magnitudes of Fourier transforms of said portion of said electrical signal corresponding to said second time period from electrodes i, and respectively, of said plurality of electrodes.

4. A method of identifying an epileptogenic zone of a subject's brain according to claim 3, wherein said connectivity matrix is a time-dependent connectivity matrix that includes said calculations for said first time period and said second time period as representations of said connectivity matrix at two times.

5. A method of identifying an epileptogenic zone of a subject's brain according to claim 4, further comprising calculating said connectivity matrix by using the formula $$A_{ij} = \int_{50Hz}^{90Hz} P_i(f)P_j(f)df$$

for an additional plurality of portions of each of said plurality of electrical signals for corresponding additional time periods to provide representations of said connectivity matrix corresponding to a plurality of times.

6. A method of identifying an epileptogenic zone of a subject's brain according to claim 5, further comprising calculating time-dependent eigenvectors corresponding to said time-dependent connectivity matrix.

7. A method of identifying an epileptogenic zone of a subject's brain according to claim 6, further comprising converting said time-dependent eigenvectors into ranked time-dependent eigenvectors.

8. A method of identifying an epileptogenic zone of a subject's brain according to claim 7, further comprising forming a correlation matrix based on said ranked time-dependent eigenvectors.

9. A method of identifying an epileptogenic zone of a subject's brain according to claim 8, further comprising identifying said cluster of electrodes based on said correlation matrix.

10. A non-transitory computer-readable medium for identifying an epileptogenic zone of a subject's brain comprising computer-executable code, said code when executed by a computer causes the computer to:
    receive a plurality of electrical signals from a corresponding plurality of surgically implanted electrodes;
    calculate a first plurality of connectivities between each pair of electrodes based on a portion of each of said plurality of electrical signals corresponding to a first time period;
    assign a rank corresponding to each electrode for said first period of time based on said first plurality of connectivities to provide a first plurality of ranks;
    calculate a second plurality of connectivities between each pair of electrodes based on a portion of each of said plurality of electrical signals corresponding to a second time period;
    assign a rank corresponding to each electrode for said second period of time based on said second plurality of connectivities to provide a second plurality of ranks;
    identify a cluster of electrodes among said plurality of electrodes based on relative changes between said first plurality of ranks from said first time period and said second plurality of ranks at said second time period;
    identify said epileptogenic zone based on said cluster of electrodes; and
    display said identified epileptogenic zone.

11. A computer-readable medium according to claim 10, wherein said calculating said first plurality of connectivities calculates a connectivity matrix by using the formula $$A_{ij} = \int_{50Hz}^{90Hz} P_i(f)P_j(f)df$$

where $P_i$, $P_j$ are magnitudes of Fourier transforms of said portion of said electrical signal corresponding to said first time period from electrodes i, and respectively, of said plurality of electrodes.

12. A computer-readable medium according to claim 11, wherein said calculating said second plurality of connectivities calculates a connectivity matrix by using the formula $$A_{ij} = \int_{50Hz}^{90Hz} P_i(f)P_j(f)df$$

where $P_i$, $P_j$ are magnitudes of Fourier transforms of said portion of said electrical signal corresponding to said second time period from electrodes i, and respectively, of said plurality of electrodes.

13. A computer-readable medium according to claim 12, wherein said connectivity matrix is a time-dependent connectivity matrix that includes said calculations for said first time period and said second time period as representations of said connectivity matrix at two times.

14. A computer-readable medium according to claim 13, wherein said code further causes said computer to calculate said connectivity matrix by using the formula $$A_{ij} = \int_{50Hz}^{90Hz} P_i(f)P_j(f)df$$

for an additional plurality of portions of each of said plurality of electrical signals for corresponding additional time periods to provide representations of said connectivity matrix corresponding to a plurality of times.

15. A computer-readable medium according to claim 14, wherein said code further causes said computer to calculate time-dependent eigenvectors corresponding to said time-dependent connectivity matrix.

16. A computer-readable medium according to claim 15, wherein said code further causes said computer to convert said time-dependent eigenvectors into ranked time-dependent eigenvectors.

17. A computer-readable medium according to claim 16, wherein said code further causes said computer to form a correlation matrix based on said ranked time-dependent eigenvectors.

18. A computer-readable medium according to claim 17, wherein said code further causes said computer to identify said cluster of electrodes based on said correlation matrix.

19. A system for identifying an epileptogenic zone of a subject's brain comprising a computer configured to:
    receive a plurality of electrical signals from a corresponding plurality of surgically implanted electrodes;
    calculate a first plurality of connectivities between each pair of electrodes based on a portion of each of said plurality of electrical signals corresponding to a first time period;
    assign a rank corresponding to each electrode for said first period of time based on said first plurality of connectivities to provide a first plurality of ranks;
    calculate a second plurality of connectivities between each pair of electrodes based on a portion of each of said plurality of electrical signals corresponding to a second time period;
    assign a rank corresponding to each electrode for said second period of time based on said second plurality of connectivities to provide a second plurality of ranks;
    identify a cluster of electrodes among said plurality of electrodes based on relative changes between said first plurality of ranks from said first time period and said second plurality of ranks at said second time period;
    identify said epileptogenic zone based on said cluster of electrodes; and
    display said identified epileptogenic zone.

20. A system according to claim 19, wherein said calculating said first plurality of connectivities calculates a connectivity matrix by using the formula $$A_{ij} = \int_{50Hz}^{90Hz} P_i(f)P_j(f)df$$

where $P_i$, $P_j$ are magnitudes of Fourier transforms of said portion of said electrical signal corresponding to said first time period from electrodes i, and respectively, of said plurality of electrodes.

21. A system according to claim 20, wherein said calculating said second plurality of connectivities calculates a connectivity matrix by using the formula $$A_{ij} = \int_{50Hz}^{90Hz} P_i(f)P_j(f)df$$

where $P_i$, $P_j$ are magnitudes of Fourier transforms of said portion of said electrical signal corresponding to said second time period from electrodes i, and respectively, of said plurality of electrodes.

22. A system according to claim 21, wherein said connectivity matrix is a time-dependent connectivity matrix that includes said calculations for said first time period and said second time period as representations of said connectivity matrix at two times.

23. A system according to claim 22, wherein said computer is further configured to calculate said connectivity matrix by using the formula $$A_{ij} = \int_{50Hz}^{90Hz} P_i(f)P_j(f)df$$

for an additional plurality of portions of each of said plurality of electrical signals for corresponding additional time periods to provide representations of said connectivity matrix corresponding to a plurality of times.

24. A system according to claim 23, wherein said computer is further configured to calculate time-dependent eigenvectors corresponding to said time-dependent connectivity matrix.

25. A system according to claim 24, wherein said computer is further configured to convert said time-dependent eigenvectors into ranked time-dependent eigenvectors.

26. A system according to claim 25, wherein said computer is further configured to form a correlation matrix based on said ranked time-dependent eigenvectors.

27. A system according to claim 26, wherein said computer is further configured to identify said cluster of electrodes based on said correlation matrix.

\* \* \* \* \*